(12) United States Patent
Zhang et al.

(10) Patent No.: US 9,365,843 B2
(45) Date of Patent: Jun. 14, 2016

(54) POLYPEPTIDES HAVING CELLULOLYTIC ENHANCING ACTIVITY AND POLYNUCLEOTIDES ENCODING SAME

(71) Applicant: Novozymes, Inc., Davis, CA (US)

(72) Inventors: Yu Zhang, Beijing (CN); Junxin Duan, Beijing (CN); Lan Tang, Beijing (CN); Wenping Wu, Beijing (CN)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 14/707,660

(22) Filed: May 8, 2015

(65) Prior Publication Data

US 2015/0240224 A1 Aug. 27, 2015

Related U.S. Application Data

(62) Division of application No. 13/979,223, filed as application No. PCT/CN2012/071525 on Feb. 23, 2012, now Pat. No. 9,051,376.

(60) Provisional application No. 61/471,423, filed on Apr. 4, 2011.

(30) Foreign Application Priority Data

Feb. 23, 2011 (WO) ............... PCT/CN2011/071208

(51) Int. Cl.
| | |
|---|---|
| *C12N 9/42* | (2006.01) |
| *C12P 13/04* | (2006.01) |
| *C12P 5/02* | (2006.01) |
| *C12P 7/02* | (2006.01) |
| *C12P 5/00* | (2006.01) |
| *C07K 14/37* | (2006.01) |
| *C12P 19/14* | (2006.01) |

(52) U.S. Cl.
CPC .............. *C12N 9/2437* (2013.01); *C07K 14/37* (2013.01); *C12N 9/2434* (2013.01); *C12P 5/002* (2013.01); *C12P 5/02* (2013.01); *C12P 5/026* (2013.01); *C12P 7/02* (2013.01); *C12P 13/04* (2013.01); *C12P 19/14* (2013.01); *C12P 2201/00* (2013.01); *C12P 2203/00* (2013.01); *C12Y 302/01004* (2013.01); *Y02E 50/343* (2013.01); *Y02P 20/52* (2015.11)

(58) Field of Classification Search
None
See application file for complete search history.

(56) References Cited

FOREIGN PATENT DOCUMENTS

| | | |
|---|---|---|
| WO | 2005/074647 A2 | 8/2005 |
| WO | 2005/074656 A2 | 8/2005 |
| WO | 2007/089290 A2 | 8/2007 |
| WO | 2008/148131 A1 | 12/2008 |
| WO | 2008/151043 A1 | 12/2008 |
| WO | 2009/085859 A2 | 7/2009 |
| WO | 2009/085864 A2 | 7/2009 |
| WO | 2009/085868 A1 | 7/2009 |
| WO | 2009/085935 A2 | 7/2009 |
| WO | 2010/065830 A1 | 6/2010 |
| WO | 2010/138754 A1 | 12/2010 |
| WO | 2011/005867 A1 | 1/2011 |
| WO | 2011/035027 A2 | 3/2011 |
| WO | 2011/039319 A1 | 4/2011 |
| WO | 2011/041397 A1 | 4/2011 |
| WO | 2011/041504 A1 | 4/2011 |
| WO | 2012119302 A2 | 8/2013 |

OTHER PUBLICATIONS

Galagan et al., Genbank Accession No. XP_661115 (2008).
Wortman et al., Genbank Accession No. CBF76006 (2009).
Markku et al, 1997, Eur J Biochem 249(2), 584-591.
Chica et al, 2005, Curr Op Biotechnol 16(4), 378-384.
Harris et al, 2010, Biochem 49, 3305-3316.
Sen et al, 2007, Appl Biochem Biotechnol 143(3), 212-223.

*Primary Examiner* — Christian Fronda
(74) *Attorney, Agent, or Firm* — Robert L. Starnes

(57) ABSTRACT

The present invention relates to isolated polypeptides having cellulolytic enhancing activity and isolated polynucleotides encoding the polypeptides. The invention also relates to nucleic acid constructs, vectors, and host cells comprising the polynucleotides as well as methods of producing and using the polypeptides.

39 Claims, 6 Drawing Sheets

```
Aligned_sequences:
# 1: seq2
# 2: seq4
# Identity:      119/311 (38.3%)

Seq2       1 RCTVSDLVINCVYPCWLPGRDPYNP---DPPICVCKRTPNLDNCPVTPS        47
             |.|.|.....|......||.||..|    .|..|.|.|......|...|
Seq4       1 RCPVTFITVLGDNRFIY-PGFCP3TPKEVPPSLSVARSTSASDQGYMSBS        49

Seq2      48 KAS--TDAVICKKEATPAKGHVSVK&GDKIYIQWQPNPWPDSHKCPVLDY        95
             .||   ..|||..|.|.|....|||.....|.||.|...|.|..|||||
Seq4      50 NASYHSKDFICHRNAKPAPDAAQVHAGDKVQLHWTQWPGPEDHQGPILDY        99

Seq2      96 LAPCNGPCESVDKTSLPFPKIDGVCLIDGSSPGYWADDELIANQNQWLV        145
             ||.|||||.|.|..||..||  ||.   .|.|.|.|.|...||.|||.|
Seq4     100 LASCNGPCSBVEPASLKWTKIDEABRP----PDSTRATDLLPNKDNTWNV        145

Seq2     146 QIPSDIKPCBYVLRSBIXLHSAGH&DDAQLYPQCPNLBITSKGTVBPSG        195
             .|.||.||.||||.||.||||||..|.||||....|||.||.|||.|.|
Seq4     146 TIPSDLAPGBYVLRNEIIALHSAPNMGGAQHYMQCVNLNVTGTGHRBLQG        195

Seq2     196 VPATEPYSPDDPGILVNIY--SPLSTYEVPGPSLIPQAVQIE--QSSSAI        241
             |.|.|||.|||.||.|.|.  ..|.|.|.|||.|.......|  .|.|.|
Seq4     196 VSLAEPYSPTDPGILIBVWQTGSLGSYHIPGPTLLAADTGNLGGHSAGST        245

Seq2     242 TAT----GTPTPA----------------------------------        260
             .||    .|.|.|
Seq4     246 LATVTSRPLSTPSDAMPGRGSYGAISPPLKPAKGFHPVCNARFRHGSTFT        295

Seq2     260 --------        260

Seq4     296 LTTLVAPBART        306
```

FIG. 4

```
# Aligned_sequences: 2
# 1: seq2
# 2: seq6
# Identity:      214/252 (84.9%)

Seq2          1 HGIVEDLYINGYYTPGWLPGEGPYNPDPPIGVGWETPNLGNGPYTPSEAS     50
                ||||||||||||.||||||.||||.||-||||||||||||||||.|.|||
Seq6          1 HGPVSDLYINGVFTPGWLPTEGPYKADPPIGVGWETPNLGNGPVLPEEAS     50

Seq2         51 TDAVICHPEATPAPGHVSVKAGDKIYIQWQPNWPDSHHGPVLDYLAPCN    100
                ||||.|||||.||||.||.|||||||||||||||||.|||||||||||||
Seq6         51 TDAIVCHPEABPAPGYASVAAGDKIYIQWQPNWPESHHGPVIDYLAPCN    100

Seq2        101 GPCESVDKTSLEPYKIDGVGLIDGBSPPGTWADDELIANGRSWLVQIPED    150
                |.|.||.||||||||||||||||.||||||.|||||||||||||||||||
Seq6        101 GDCSFVNKTSLEPYKIDGVGLIDGBSPPGKWADDELIANGRSWLVQIPED    150

Seq2        151 IKPGNYVLRHEIIALHSAGNPDCAQLYPQCPRLEITGSGTVEPBGVPATB    200
                |||||||||||||||.|.|.|||||||||.|||||.||||||||||.|||
Seq6        151 IKPGNYVLRHEIIALHEAFNQNGAQIYPQCPDLQITGSGTVEPBGTPATB    200

Seq2        201 YYSPGDPGYLVDIYEPLSTTRYPSPSLIPQAVQIEQSSSAITKTGTPTPA    250
                .|||.||||||||.||.|||||.|||.|||||.||||.||.|.|||||||
Seq6        201 LYSPTDPGYLVDIYNPLSTTVVPSPTLIPQAVEIEQSSEAVTSTGTPTPA    250

Seq2        250 ..    250

Seq6        251 AA    252
```

FIG. 5

```
# Aligned_sequences: 2
# 1: seq4
# 2: seq6
# Identity:      116/311 (37.3%)
```

```
Seq4     1 SGSVTKITVLGLSNKDYPGFDPS-TPKRVPPGLDVAWSTSASDQGYNSSS   49
             ||||....:  |....|.|.|  .|......|.|.|......:...
Seq6     1 SGSVSNLVI---SGVPYRGWLPTEDFTKADPFIGVSWETPGLCSGFVLPS   47

Seq4    50 SASYRSKDFICHPNAKFAPDAAQVEAGDKVQLHWTQNPSPEDKQSPILSY   99
             .||  :..:|||.|.|..|:|||....|||..:.|..||.||.||||
Seq6    48 EAS--TDAIVCRKEAFARGYASVAAGDRIYIQWQPNPWPRSHHGPVIDY   95

Seq4   100 LASCNGPCSNVEKASLKWTKIGEAGRF----PNGTWATGLLRDSGPTWDV  145
             |.|||.||  |.|.|.|::.||..|.     |.||.|.|.|.  ||.||
Seq6    96 LAPCNGDCSTVNKTSLRWFETGGVGLIGSSEFGNWADGELIANCPGWLV  145

Seq4   146 TIPSGLAPSETYLSNEIIALHSARSMKIEAQHYMQCVSLNVTGTGHPELQG  195
             .|.|.|:|||||||||:|:|||||..|:|.|.||:|:|.|:|.|.|.|:
Seq6   146 QIPEDIKPGNYVLSHEIIALHEAPIQNGAQIYPQCPNLQITGSGTVEPEG  195

Seq4   196 VSAARFYNPTDEGILINVEQTQSLSSSEBIPSPTLLAAUTSEDGGHSASET  245
             ..|.|.|:|||||.|:||::     .|.|.|.||||.....    ...|
Seq6   196 TEATBLISPTDPSILVDXY---DSLSTTVVPSPTLIPQAVEIRQSSSA---  240

Seq4   246 LATVTSPRLSTPSDAMEGNGGYGAISPPLKPAKGFEFVCNAPFEKCSTPT  295
             ||:....||:.|
Seq6   241 ----VTATGTPTPAAA--------------------------------  252

Seq4   296 LTTLVAPPKRT  306

Seq6   252 -----------  252
```

POLYPEPTIDES HAVING CELLULOLYTIC ENHANCING ACTIVITY AND POLYNUCLEOTIDES ENCODING SAME

CROSS-REFERENCE TO RELATED APPLICATIONS

This application is a divisional application of U.S. application Ser. No. 13/979,223 filed Feb. 23, 2012, which is a 35 U.S.C. §371 national application of PCT/CN2012/071525 filed Feb. 23, 2012, which claims priority or the benefit under 35 U.S.C. §119 of PCT Application No. PCT/CN2011/071208 filed Feb. 23, 2011 and U.S. Provisional Application No. 61/471,423 filed Apr. 4, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to polypeptides having cellulolytic enhancing activity and isolated polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose covalently linked by beta-1,4 bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose. Once the cellulose is converted to glucose, the glucose is easily fermented by yeast into ethanol.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin.

WO 2005/074647, WO 2008/148131, WO 2011/035027 disclose isolated GH61 polypeptides having cellulolytic enhancing activity and the polynucleotides thereof from *Thielavia terrestris*. WO 2005/074656 and WO 2010/065830 disclose isolated GH61 polypeptides having cellulolytic enhancing activity and the polynucleotides thereof from *Thermoascus aurantiacus*. WO 2007/089290 discloses an isolated GH61 polypeptide having cellulolytic enhancing activity and the polynucleotide thereof from *Trichoderma reesei*. WO 2009/085935, WO 2009/085859, WO 2009/085864, and WO 2009/085868 disclose isolated GH61 polypeptides having cellulolytic enhancing activity and the polynucleotides thereof from *Myceliophthora thermophila*. WO 2010/138754 discloses isolated GH61 polypeptides having cellulolytic enhancing activity and the polynucleotides thereof from *Aspergillus fumigatus*. WO 2011/005867 discloses isolated GH61 polypeptides having cellulolytic enhancing activity and the polynucleotides thereof from *Penicillium pinophilum*. WO 2011/039319 discloses isolated GH61 polypeptides having cellulolytic enhancing activity and the polynucleotides thereof from *Thermoascus* sp. WO 2011/041397 discloses isolated GH61 polypeptides having cellulolytic enhancing activity and the polynucleotides thereof from *Penicillium* sp. WO 2011/041504 discloses isolated GH61 polypeptides having cellulolytic enhancing activity and the polynucleotides thereof from *Thermoascus crustaceous*. WO 2008/151043 discloses methods of increasing the activity of a GH61 polypeptide having cellulolytic enhancing activity by adding a soluble activating divalent metal cation to a composition comprising the polypeptide.

There is a need in the art for new enzymes to increase efficiency and to provide cost-effective enzyme solutions for saccharification of cellulosic material. The present invention provides GH61 polypeptides having cellulolytic enhancing activity and polynucleotides encoding the polypeptides.

SUMMARY OF THE INVENTION

The present invention relates to isolated polypeptides having cellulolytic enhancing activity selected from the group consisting of:

(a) a polypeptide having at least 70% sequence identity to the mature polypeptide of SEQ ID NO: 2, or at least 60% sequence identity to the mature polypeptide of SEQ ID NO: 4, or at least 70% sequence identity to the mature polypeptide of SEQ ID NO: 6;

(b) a polypeptide encoded by a polynucleotide that hybridizes under at least medium stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii);

(c) a polypeptide encoded by a polynucleotide having at least 70% sequence identity to the mature polypeptide of SEQ ID NO: 1, or at least 60% sequence identity to the mature polypeptide of SEQ ID NO: 3, or at least 70% sequence identity to the mature polypeptide of SEQ ID NO: 5;

(d) a variant of the mature polypeptide of SEQ ID NO: 2, SEQ ID NO: 4, or SEQ ID NO: 6 comprising a substitution, deletion, and/or insertion of one or more (e.g., several) amino acids; and (e) a fragment of the polypeptide of (a), (b), (c), or (d) that has cellulolytic enhancing activity.

The present invention also relates to isolated polynucleotides encoding polypeptides having cellulolytic enhancing activity, selected from the group consisting of:

(a) a polynucleotide encoding a polypeptide having at least 70% sequence identity to the mature polypeptide of SEQ ID NO: 2, or at least 60% sequence identity to the mature polypeptide of SEQ ID NO: 4, or at least 70% sequence identity to the mature polypeptide of SEQ ID NO: 6;

(b) a polynucleotide that hybridizes under at least medium stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii);

(c) a polynucleotide having at least 70% sequence identity to the mature polypeptide of SEQ ID NO: 1, or at least 60% sequence identity to the mature polypeptide of SEQ ID NO: 3, or at least 70% sequence identity to the mature polypeptide of SEQ ID NO: 5;

(d) a polynucleotide encoding a variant of SEQ ID NO: 2, SEQ ID NO: 4, or SEQ ID NO: 6 comprising a substitution, deletion, and/or insertion of one or more (e.g., several) amino acids of the mature polypeptide; and (e) a fragment of the polynucleotide of (a), (b), (c), or (d) that has cellulolytic enhancing activity.

The present invention also relates to nucleic acid constructs, recombinant expression vectors, recombinant host cells comprising the polynucleotides, and methods of producing the polypeptides having cellulolytic enhancing activity.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. The present also relates to such a double-stranded RNA (dsRNA) molecule, wherein optionally the dsRNA is an siRNA or an miRNA molecule.

The present invention also relates to compositions comprising the polypeptide of the present invention.

The present invention also relates to methods for degrading or converting a cellulosic material, comprising: treating the cellulosic material with an enzyme composition in the presence of a polypeptide having cellulolytic enhancing activity of the present invention. In a preferred aspect, the method further comprises recovering the degraded or converted cellulosic material.

The present invention also relates to methods of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention. In a preferred aspect, the fermenting of the cellulosic material produces a fermentation product. In one aspect, the method further comprises recovering the fermentation product from the fermentation.

The present invention also relates to plants comprising an isolated polynucleotide encoding a polypeptide having cellulolytic enhancing activity.

The present invention also relates to methods of producing a polypeptide having cellulolytic enhancing activity, comprising: (a) cultivating a transgenic plant or a plant cell comprising a polynucleotide encoding the polypeptide having cellulolytic enhancing activity under conditions conducive for production of the polypeptide; and (b) recovering the polypeptide.

The present invention further relates to an isolated polynucleotide encoding a signal peptide comprising or consisting of amino acids 1 to 22 of SEQ ID NO: 2, amino acids 1 to 21 of SEQ ID NO: 4, or amino acids 1 to 22 of SEQ ID NO: 6; to nucleic acid constructs, expression vectors, and recombinant host cells comprising the polynucleotides; and methods of producing a protein.

The present invention further relates to a whole broth formulation or cell culture composition comprising the polypeptide of the present invention.

BRIEF DESCRIPTION OF THE FIGURES

FIG. 1 shows the genomic DNA sequence and the deduced amino acid sequence of a gene encoding a *Thermomyces lanuginosus* GH61(1) polypeptide having cellulolytic enhancing activity (SEQ ID NOs: 1 and 2, respectively).

Figure 2:
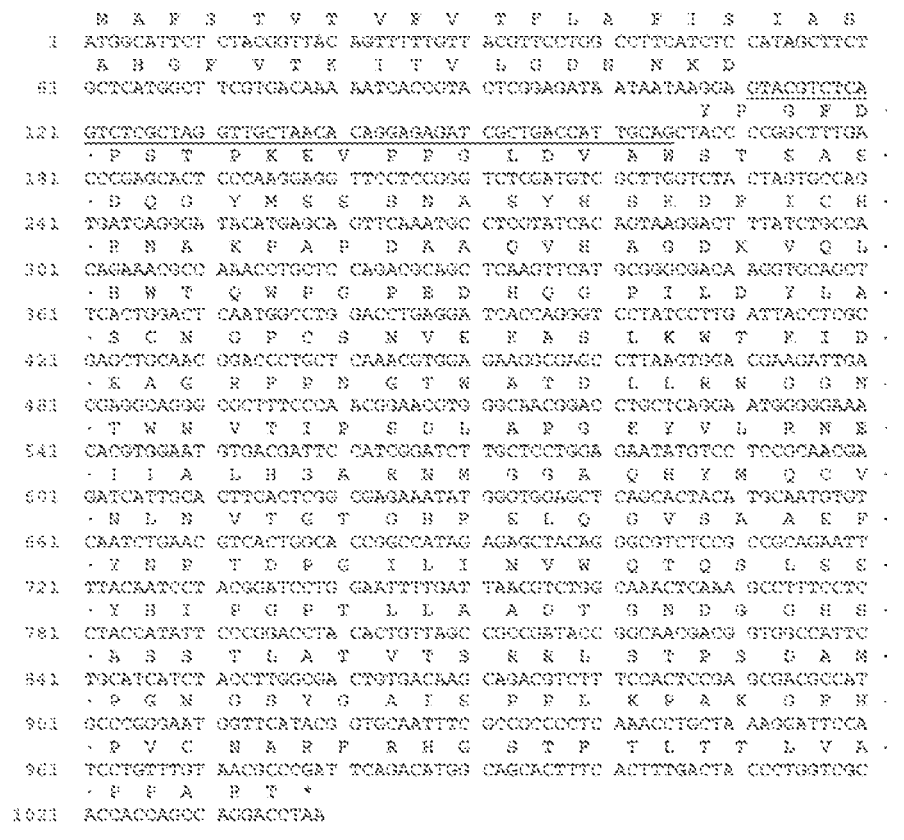

FIG. 2 shows the genomic DNA sequence and the deduced amino acid sequence of a gene encoding a *Thermomyces lanuginosus* GH61(2) polypeptide having cellulolytic enhancing activity (SEQ ID NOs: 3 and 4, respectively).

FIG. 3 shows the genomic DNA sequence and the deduced amino acid sequence of a gene encoding a *Thermomyces lanuginosus* GH61(3) polypeptide having cellulolytic enhancing activity (SEQ ID NOs: 5 and 6, respectively).

FIG. 4 shows the alignment of SEQ ID NOs: 2 and 4.

FIG. 5 shows the alignment of SEQ ID NOs: 2 and 6.

FIG. 6 shows the alignment of SEQ ID NOs: 4 and 6.

DEFINITIONS

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 30° C., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes NS, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The polypeptides having cellulolytic enhancing activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellulolytic enhancing activity of the mature polypeptide of SEQ ID NO: 2, the mature polypeptide of SEQ ID NO: 4 or the mature polypeptide of SEQ ID NO: 6.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune, FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 30° C., 50° C., 55° C., or 60° C., and pH, e.g., 5.0 or 5.5.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methyl-glucuronic acid per minute at pH 5, 40° C.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Pretreated corn stover: The term "PCS" or "Pretreated Corn Stover" means a cellulosic material derived from corn stover by treatment with heat and dilute sulfuric acid, alkaline pretreatment, or neutral pretreatment.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). The polypeptide of the present invention may be used in industrial applications in the form of a fermentation broth product, that is, the polypeptide of the present invention is a component of a fermentation broth used as a product in industrial applications (e.g., ethanol production). The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subjected to one or more purification (including filtration) steps to remove or reduce one more components of a fermentation process. Accordingly, an isolated substance may be present in such a fermentation broth product.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 23 to 272 of SEQ ID NO: 2 based on the SignalP program (Nielsen et al., 1997, Protein Engineering 10: 1-6) that predicts amino acids 1 to 22 of SEQ ID NO: 2 are a signal peptide. In another aspect, the mature polypeptide is amino acids 22 to 327 of SEQ ID NO: 4 based on the SignalP program that predicts amino acids 1 to 21 of SEQ ID NO: 4 are a signal peptide. In another aspect, the mature polypeptide is amino acids 23 to 274 of SEQ ID NO: 6 based on the SignalP program that predicts amino acids 1 to 22 of SEQ ID NO: 6 are a signal peptide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 67 to 869 of SEQ ID NO: 1 based on the SignalP program (Nielsen et al., 1997, supra) that predicts nucleotides 1 to 66 of SEQ ID NO: 1 encode a signal peptide. In another aspect, the mature polypeptide coding sequence is nucleotides 64 to 1036 of SEQ ID NO: 3 based on the SignalP program that predicts nucleotides 1 to 63 of SEQ ID NO: 3 encode a signal peptide. In one aspect, the mature polypeptide coding sequence is nucleotides 67 to 878 of SEQ ID NO: 5 based on the SignalP program that predicts nucleotides 1 to 66 of SEQ ID NO: 5 encode a signal peptide.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0, 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0, 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein having an E value (or expectancy score) of less than 0.001 in a tfasty search (Pearson, W. R., 1999, in Bioinformatics Methods and Protocols, S. Misener and S. A. Krawetz, ed., pp. 185-219) with the Thermomyces lanuginosus polypeptide having cellulolytic enhancing activity of SEQ ID NO: 2, SEQ ID NO: 4, or SEQ ID NO: 6 or the mature polypeptide thereof.

Polypeptide fragment: The term "polypeptide fragment" is defined herein as a polypeptide having one or more (e.g., several) amino acids deleted from the amino and/or carboxyl terminus of the mature polypeptide of SEQ ID NO: 2, SEQ ID NO: 4, or SEQ ID NO: 6; or a homologous sequence thereof; wherein the fragment has cellulolytic enhancing activity. In a preferred aspect, a fragment contains at least 190 amino acid residues, more preferably at least 200 amino acid residues, and most preferably at least 210 amino acid residues, of the mature polypeptide of SEQ ID NO: 2 or a homologous sequence thereof. In another preferred aspect, a fragment contains at least 270 amino acid residues, more preferably at least 290 amino acid residues, and most preferably at least 310 amino acid residues, of the mature polypeptide of SEQ ID NO: 4 or a homologous sequence thereof. In another preferred aspect, a fragment contains at least 190 amino acid residues, more preferably at least 200 amino acid residues, and most preferably at least 210 amino acid residues, of the mature polypeptide of SEQ ID NO: 6 or a homologous sequence thereof.

Subsequence: The term "subsequence" is defined herein as a nucleotide sequence having one or more (e.g., several) nucleotides absent from the 5' and/or 3' end of the mature polypeptide coding sequence of SEQ ID NO: 1, SEQ ID NO: 3, or SEQ ID NO: 5; or a homologous sequence thereof; wherein the subsequence encodes a polypeptide fragment having cellulolytic enhancing activity. In a preferred aspect, a subsequence contains at least 570 nucleotides, more preferably at least 600 nucleotides, and most preferably at least 630 nucleotides of the mature polypeptide coding sequence of SEQ ID NO: 1 or a homologous sequence thereof. In another preferred aspect, a subsequence contains at least 810 nucleotides, more preferably at least 870 nucleotides, and most preferably at least 930 nucleotides of the mature polypeptide coding sequence of SEQ ID NO: 3 or a homologous sequence thereof. In another preferred aspect, a subsequence contains at least 570 nucleotides, more preferably at least 600 nucleotides, and most preferably at least 630 nucleotides of the mature polypeptide coding sequence of SEQ ID NO: 5 or a homologous sequence thereof.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA. These steps include the removal of intron sequences by a process called splicing. cDNA derived from mRNA lacks, therefore, any intron sequences.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Modification: The term "modification" means herein any chemical modification of the polypeptide comprising or consisting of the mature polypeptide of SEQ ID NO: 2, SEQ ID NO: 4, or SEQ ID NO: 6; or a homologous sequence thereof; as well as genetic manipulation of the DNA encoding such a polypeptide. The modification can be a substitution, a deletion and/or an insertion of one or more (e.g., several) amino acids as well as replacements of one or more (e.g., several) amino acid side chains.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours.

The carrier material is finally washed three times each for 15 minutes using 2×SSC, 0.2% SDS at 45° C.

DETAILED DESCRIPTION OF THE INVENTION

Polypeptides Having Cellulolytic Enhancing Activity

In a first aspect, the present invention relates to isolated polypeptides comprising amino acid sequences having a degree of identity to the mature polypeptide of SEQ ID NO: 2 of preferably at least 70%, at least 75%, at least 80%, at least 81%, at least 82%, at least 83%, at least 84%, at least 85%, at least 86%, at least 87%, at least 88%, or at least 89%, more preferably at least 90%, at least 91%, at least 92%, at least 93%, at least 94%, at least 95%, and most preferably at least 96%, at least 97%, at least 98%, at least 99%, or 100%, which have cellulolytic enhancing activity (hereinafter "homologous polypeptides"). In a preferred aspect, the homologous polypeptides comprise amino acid sequences that differ by preferably ten amino acids, by nine amino acids, by eight amino acids, even preferably by seven amino acids, by six amino acids, more preferably by five amino acids, by four amino acids, even more preferably by three amino acids, most preferably by two amino acids, and even most preferably by one amino acid from the mature polypeptide of SEQ ID NO: 2.

In a preferable embodiment, the homologous polypeptide of SEQ ID NO: 2 can be SEQ ID NO: 6. The mature polypeptide of SEQ ID NO: 2 has a degree of identity to the mature polypeptide of SEQ ID NO: 6 of 84.9%.

In another first aspect, the present invention relates to isolated polypeptides comprising amino acid sequences having a degree of identity to the mature polypeptide of SEQ ID NO: 4 of preferably at least 60%, at least 65%, at least 70%, at least 75%, even preferably at least 80%, more preferably at least 81%, at least 82%, at least 83%, at least 84%, at least 85%, at least 86%, at least 87%, at least 88%, at least 89%, even more preferably at least 90%, at least 91%, at least 92%, at least 93%, at least 94%, most preferably at least 95%, and even most preferably at least 96%, at least 97%, at least 98%, at least 99%, or 100%, which have cellulolytic enhancing activity (hereinafter "homologous polypeptides"). In a preferred aspect, the homologous polypeptides comprise amino acid sequences that differ by preferably ten amino acids, by nine amino acids, by eight amino acids, even preferably by seven amino acids, by six amino acids, more preferably by five amino acids, by four amino acids, even more preferably by three amino acids, most preferably by two amino acids, and even most preferably by one amino acid from the mature polypeptide of SEQ ID NO: 4.

In another first aspect, the present invention relates to isolated polypeptides comprising amino acid sequences having a degree of identity to the mature polypeptide of SEQ ID NO: 6 of preferably at least 70%, at least 75%, at least 80%, at least 81%, at least 82%, at least 83%, at least 84%, at least 85%, at least 86%, at least 87%, at least 88%, at least 89%, more preferably at least 90%, at least 91%, at least 92%, at least 93%, at least 94%, most preferably at least 95%, and even most preferably at least 96%, at least 97%, at least 98%, at least 99%, or 100%, which have cellulolytic enhancing activity (hereinafter "homologous polypeptides"). In a preferred aspect, the homologous polypeptides comprise amino acid sequences that differ by ten amino acids, by nine amino acids, by eight amino acids, even preferably by seven amino acids, by six amino acids, more preferably by five amino acids, by four amino acids, even more preferably by three amino acids, most preferably by two amino acids, and even most preferably by one amino acid from the mature polypeptide of SEQ ID NO: 6.

In a preferable embodiment, the homologous polypeptide of SEQ ID NO: 6 can be SEQ ID NO: 2. The mature polypeptide of SEQ ID NO: 6 has a degree of identity to SEQ ID NO: 2 of 84.9%.

A polypeptide of the present invention preferably comprises the amino acid sequence of SEQ ID NO: 2 or an allelic variant thereof; or a fragment thereof having cellulolytic enhancing activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 23 to 272 of SEQ ID NO: 2, or an allelic variant thereof; or a fragment thereof having cellulolytic enhancing activity. In another preferred aspect, the polypeptide comprises amino acids 23 to 272 of SEQ ID NO: 2. In another preferred aspect, the polypeptide consists of the amino acid sequence of SEQ ID NO: 2 or an allelic variant thereof; or a fragment thereof having cellulolytic enhancing activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 23 to 272 of SEQ ID NO: 2 or an allelic variant thereof; or a fragment thereof having cellulolytic enhancing activity. In another preferred aspect, the polypeptide consists of amino acids 23 to 272 of SEQ ID NO: 2.

A polypeptide of the present invention preferably comprises the amino acid sequence of SEQ ID NO: 4 or an allelic variant thereof; or a fragment thereof having cellulolytic enhancing activity. In a preferred aspect, the polypeptide comprises the amino acid sequence of SEQ ID NO: 4. In another preferred aspect, the polypeptide comprises the mature polypeptide of SEQ ID NO: 4. In another preferred aspect, the polypeptide comprises amino acids 22 to 327 of SEQ ID NO: 4, or an allelic variant thereof; or a fragment thereof having cellulolytic enhancing activity. In another preferred aspect, the polypeptide comprises amino acids 22 to 327 of SEQ ID NO: 4. In another preferred aspect, the polypeptide consists of the amino acid sequence of SEQ ID NO: 4 or an allelic variant thereof; or a fragment thereof having cellulolytic enhancing activity. In another preferred aspect, the polypeptide consists of the amino acid sequence of SEQ ID NO: 4. In another preferred aspect, the polypeptide consists of the mature polypeptide of SEQ ID NO: 4. In another preferred aspect, the polypeptide consists of amino acids 22 to 327 of SEQ ID NO: 4 or an allelic variant thereof; or a fragment thereof having cellulolytic enhancing activity. In another preferred aspect, the polypeptide consists of amino acids 22 to 327 of SEQ ID NO: 4.

A polypeptide of the present invention preferably comprises the amino acid sequence of SEQ ID NO: 6 or an allelic variant thereof; or a fragment thereof having cellulolytic enhancing activity. In a preferred aspect, the polypeptide comprises the amino acid sequence of SEQ ID NO: 6. In another preferred aspect, the polypeptide comprises the mature polypeptide of SEQ ID NO: 6. In another preferred aspect, the polypeptide comprises amino acids 23 to 274 of SEQ ID NO: 6, or an allelic variant thereof; or a fragment thereof having cellulolytic enhancing activity. In another preferred aspect, the polypeptide comprises amino acids 23 to 274 of SEQ ID NO: 6. In another preferred aspect, the polypeptide consists of the amino acid sequence of SEQ ID NO: 6 or an allelic variant thereof; or a fragment thereof having cellulolytic enhancing activity. In another preferred aspect, the polypeptide consists of the amino acid sequence of SEQ ID NO: 6. In another preferred aspect, the polypeptide consists of the mature polypeptide of SEQ ID NO: 6. In another preferred aspect, the polypeptide consists of amino acids 23 to 274 of SEQ ID NO: 6 or an allelic variant thereof; or a fragment thereof having cellulolytic enhancing activity. In another preferred aspect, the polypeptide consists of amino acids 23 to 274 of SEQ ID NO: 6.

In a second aspect, the present invention relates to isolated polypeptides having cellulolytic enhancing activity that are encoded by polynucleotides that hybridize under medium stringency conditions, or medium-high stringency conditions, preferably high stringency conditions and more preferably very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

In another second aspect, the present invention relates to isolated polypeptides having cellulolytic enhancing activity that are encoded by polynucleotides that hybridize under medium stringency conditions, or medium-high stringency conditions, or preferably high stringency conditions and more preferably very high stringency conditions with (i) the mature polypeptide coding sequence of SEQ ID NO: 3, (ii) the cDNA sequence contained in the mature polypeptide coding sequence of SEQ ID NO: 3, or (iii) a full-length complementary strand of (i) or (ii).

In another second aspect, the present invention relates to isolated polypeptides having cellulolytic enhancing activity that are encoded by polynucleotides that hybridize under medium stringency conditions, or medium-high stringency conditions, preferably high stringency conditions and more preferably very high stringency conditions with (i) the mature polypeptide coding sequence of SEQ ID NO: 5, (ii) the cDNA sequence contained in the mature polypeptide coding sequence of SEQ ID NO: 5, or (iii) a full-length complementary strand of (i) or (ii).

The polynucleotide of SEQ ID NO: 1, SEQ ID NO: 3, or SEQ ID NO: 5; or a subsequence thereof; as well as the amino acid sequence of SEQ ID NO: 2, SEQ ID NO: 4, or SEQ ID NO: 6; or a fragment thereof; may be used to design nucleic acid probes to identify and clone DNA encoding polypeptides having cellulolytic enhancing activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, preferably at least 25, more preferably at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, or SEQ ID NO: 5, or a subsequence thereof, the carrier material is preferably used in a Southern blot.

For purposes of the present invention, hybridization indicates that the polynucleotide hybridizes to a labeled nucleic acid probe corresponding to (i) SEQ ID NO: 1, SEQ ID NO: 3, or SEQ ID NO: 5; (ii) the mature polypeptide coding sequence of SEQ ID NO: 1, SEQ ID NO: 3, or SEQ ID NO: 5; (iii) the cDNA sequence contained in the mature polypeptide coding sequence of SEQ ID NO: 1, SEQ ID NO: 3, or SEQ ID NO: 5; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another preferred aspect, the nucleic acid probe is nucleotides 67 to 869 of SEQ ID NO: 1. In another preferred aspect, the nucleic acid probe is a polynucleotide that encodes the polypeptide of SEQ ID NO: 2, or a subsequence thereof. In another preferred aspect, the nucleic acid probe is SEQ ID NO: 1. In another aspect, the nucleic acid probe is the polynucleotide contained in plasmid pGH61_664 which is contained in *E. coli* CGMCC 4601, wherein the polynucleotide thereof encodes a polypeptide having cellulolytic enhancing activity. In another preferred aspect, the nucleic acid probe is the mature polypeptide coding region contained in plasmid pGH61_664 which is contained in *E. coli* CGMCC 4601.

In one aspect, the nucleic acid probe is the mature polypeptide coding sequence of SEQ ID NO: 3. In another preferred aspect, the nucleic acid probe is nucleotides 64 to 1036 of SEQ ID NO: 3. In another preferred aspect, the nucleic acid probe is a polynucleotide that encodes the polypeptide of SEQ ID NO: 4, or a subsequence thereof. In another preferred aspect, the nucleic acid probe is SEQ ID NO: 3. In another aspect, the nucleic acid probe is the polynucleotide contained in plasmid pGH61_1590 which is contained in *E. coli* CGMCC 4602, wherein the polynucleotide thereof encodes a polypeptide having cellulolytic enhancing activity. In another preferred aspect, the nucleic acid probe is the mature polypeptide coding region contained in plasmid pGH61_1590 which is contained in *E. coli* CGMCC 4602.

In one aspect, the nucleic acid probe is the mature polypeptide coding sequence of SEQ ID NO: 5. In another preferred aspect, the nucleic acid probe is nucleotides 67 to 878 of SEQ ID NO: 5. In another preferred aspect, the nucleic acid probe is a polynucleotide that encodes the polypeptide of SEQ ID NO: 6, or a subsequence thereof. In another preferred aspect, the nucleic acid probe is SEQ ID NO: 5. In another aspect, the nucleic acid probe is the polynucleotide contained in plasmid pGH61_4950 which is contained in *E. coli* CGMCC 4600, wherein the polynucleotide thereof encodes a polypeptide having cellulolytic enhancing activity. In another preferred aspect, the nucleic acid probe is the mature polypeptide coding region contained in plasmid pGH61_4950 which is contained in *E. coli* CGMCC 4600.

In another embodiment, the present invention relates to isolated polypeptides having cellulolytic enhancing activity encoded by polynucleotides comprising or consisting of nucleotide sequences that have a degree of sequence identity to the mature polypeptide coding sequence of SEQ ID NO: 1 of at least 70%, e.g., at least 75%, at least 80%, at least 81%, at least 82%, at least 83%, at least 84%, at least 85%, at least 86%, at least 87%, at least 88%, at least 89%, more preferably at least 90%, at least 91%, at least 92%, at least 93%, at least 94%, more preferably at least 95%, and most preferably at least 96%, at least 97%, at least 98%, at least 99%, or 100%, which encode a polypeptide having cellulolytic enhancing activity.

In another embodiment, the present invention relates to isolated polypeptides having cellulolytic enhancing activity encoded by polynucleotides comprising or consisting of nucleotide sequences that have a degree of sequence identity to the mature polypeptide coding sequence of SEQ ID NO: 3 of preferably at least 60%, at least 65%, at least 70%, at least 75%, even preferably at least 80%, at least 81%, at least 82%, at least 83%, at least 84%, at least 85%, at least 86%, at least 87%, at least 88%, at least 89%, even more preferably at least 90%, at least 91%, at least 92%, at least 93%, at least 94%, most preferably at least 95%, and even most preferably at least 96%, at least 97%, at least 98%, at least 99%, or 100%, which encode a polypeptide having cellulolytic enhancing activity.

In another embodiment, the present invention relates to isolated polypeptides having cellulolytic enhancing activity encoded by polynucleotides comprising or consisting of nucleotide sequences that have a degree of identity to the mature polypeptide coding sequence of SEQ ID NO: 5 of at least 70%, at least 75%, at least 80%, at least 81%, at least 82%, at least 83%, at least 84%, at least 85%, at least 86%, at least 87%, at least 88%, at least 89%, more preferably at least 90%, at least 91%, at least 92%, at least 93%, at least 94%, most preferably at least 95%, and even most preferably at least 96%, at least 97%, at least 98%, at least 99%, or 100%, which encode a polypeptide having cellulolytic enhancing activity.

In another embodiment, the present invention relates to variants of the mature polypeptide of SEQ ID NO: 2, SEQ ID NO: 4, or SEQ ID NO: 6 comprising a substitution, deletion, and/or insertion of one or more (e.g., several) amino acids. In an embodiment, the number of amino acid substitutions, deletions and/or insertions introduced into the mature polypeptide of SEQ ID NO: 2, SEQ ID NO: 4, or SEQ ID NO: 6 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/ Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The sequence identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry. 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides.

Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Cellulolytic Enhancing Activity

A polypeptide having cellulolytic enhancing activity of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

The polypeptide having cellulolytic enhancing activity of the present invention may also be a fungal polypeptide. In one aspect, the polypeptide is a *Thermomyces* polypeptide. In another aspect, the polypeptide is *Thermomyces lanuginosus* polypeptide having cellulolytic enhancing activity. In a most preferred aspect, the polypeptide is a *Thermomyces lanuginosus* strain NN044973 polypeptide having cellulolytic enhancing activity.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide having cellulolytic enhancing activity of the present invention.

In a preferred aspect, the nucleotide sequence comprises or consists of SEQ ID NO: 1. In another more preferred aspect, the nucleotide sequence comprises or consists of the sequence contained in plasmid pGH61_664 which is contained in *E. coli* CGMCC 4601. In another preferred aspect, the nucleotide sequence comprises or consists of the mature polypeptide coding sequence of SEQ ID NO: 1. In another preferred aspect, the nucleotide sequence comprises or consists of nucleotides 67 to 869 of SEQ ID NO: 1. In another more preferred aspect, the nucleotide sequence comprises or consists of the mature polypeptide coding sequence contained in plasmid pGH61_664 which is contained in *E. coli* CGMCC 4601. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have cellulolytic enhancing activity.

In another preferred aspect, the nucleotide sequence comprises or consists of SEQ ID NO: 3. In another more preferred aspect, the nucleotide sequence comprises or consists of the sequence contained in plasmid pGH61_1590 which is contained in *E. coli* CGMCC 4602. In another preferred aspect, the nucleotide sequence comprises or consists of the mature polypeptide coding sequence of SEQ ID NO: 3. In another preferred aspect, the nucleotide sequence comprises or consists of nucleotides 64 to 1036 of SEQ ID NO: 3. In another more preferred aspect, the nucleotide sequence comprises or consists of the mature polypeptide coding sequence contained in plasmid pGH61_1590 which is contained in *E. coli* CGMCC 4602. The present invention also encompasses nucleotide sequences that encode polypeptides comprising or consisting of the amino acid sequence of SEQ ID NO: 4 or the mature polypeptide thereof, which differ from SEQ ID NO: 3 or the mature polypeptide coding sequence thereof by virtue of the degeneracy of the genetic code. The present invention also relates to subsequences of SEQ ID NO: 3 that encode fragments of SEQ ID NO: 4 that have cellulolytic enhancing activity.

In another preferred aspect, the nucleotide sequence comprises or consists of SEQ ID NO: 5. In another more preferred aspect, the nucleotide sequence comprises or consists of the sequence contained in plasmid pGH61_4950 which is contained in *E. coli* CGMCC 4600. In another preferred aspect, the nucleotide sequence comprises or consists of the mature polypeptide coding sequence of SEQ ID NO: 5. In another preferred aspect, the nucleotide sequence comprises or consists of nucleotides 67 to 878 of SEQ ID NO: 5. In another more preferred aspect, the nucleotide sequence comprises or consists of the mature polypeptide coding sequence contained in plasmid pGH61_4950 which is contained in *E. coli* CGMCC 4600. The present invention also encompasses nucleotide sequences that encode polypeptides comprising or consisting of the amino acid sequence of SEQ ID NO: 6 or the mature polypeptide thereof, which differ from SEQ ID NO: 5 or the mature polypeptide coding sequence thereof by virtue of the degeneracy of the genetic code. The present invention also relates to subsequences of SEQ ID NO: 5 that encode fragments of SEQ ID NO: 6 that have cellulolytic enhancing activity.

The present invention also relates to mutant polynucleotides comprising or consisting of at least one mutation in the mature polypeptide coding sequence of SEQ ID NO: 1, SEQ ID NO: 3, or SEQ ID NO: 5, in which the mutant nucleotide sequence encodes the mature polypeptide of SEQ ID NO: 2, SEQ ID NO: 4, or SEQ ID NO: 6, respectively.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and nucleic acid sequence-based amplification (NASBA) may be used. The polynucleotides may be cloned from a strain of *Thermomyces*, or a related organism and thus, for example, may be an allelic or species variant of the polypeptide encoding region of the polynucleotide.

The present invention also relates to isolated polynucleotides comprising or consisting of nucleotide sequences that have a degree of sequence identity to the mature polypeptide coding sequence of SEQ ID NO: 1 of at least 70%, at least 75%, at least 80%, at least 81%, at least 82%, at least 83%, at least 84%, at least 85%, at least 86%, at least 87%, at least 88%, at least 89%, more preferably at least 90%, at least 91%, at least 92%, at least 93%, at least 94%, more preferably at least 95%, and most preferably at least 96%, at least 97%, at least 98%, at least 99%, or 100%, which encode a polypeptide having cellulolytic enhancing activity.

The present invention also relates to isolated polynucleotides comprising or consisting of nucleotide sequences that have a degree of sequence identity to the mature polypeptide coding sequence of SEQ ID NO: 3 of preferably at least 60%, at least 65%, at least 70%, at least 75%, even preferably at least 80%, at least 81%, at least 82%, at least 83%, at least 84%, at least 85%, at least 86%, at least 87%, at least 88%, at least 89%, even more preferably at least 90%, at least 91%, at least 92%, at least 93%, at least 94%, most preferably at least 95%, and even most preferably at least 96%, at least 97%, at least 98%, at least 99%, or 100%, which encode a polypeptide having cellulolytic enhancing activity.

The present invention also relates to isolated polynucleotides comprising or consisting of nucleotide sequences that have a degree of identity to the mature polypeptide coding sequence of SEQ ID NO: 5 of at least 70%, at least 75%, at least 80%, at least 81%, at least 82%, at least 83%, at least 84%, at least 85%, at least 86%, at least 87%, at least 88%, at least 89%, more preferably at least 90%, at least 91%, at least 92%, at least 93%, at least 94%, most preferably at least 95%, and even most preferably at least 96%, at least 97%, at least 98%, at least 99%, or 100%, which encode a polypeptide having cellulolytic enhancing activity.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the polynucleotide presented as the mature polypeptide coding sequence of SEQ ID NO: 1, SEQ ID NO: 3, or SEQ ID NO: 5, or the cDNA sequences thereof, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for cellulolytic enhancing activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under at least medium stringency conditions, or at least medium-high stringency conditions, preferably high stringency conditions and more preferably very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii); or allelic variants and subsequences thereof (Sambrook et al., 1989, supra), as defined herein.

The present invention also relates to isolated polynucleotides obtained by (a) hybridizing a population of DNA under at least medium stringency conditions, or at least medium-high stringency conditions, or high or very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii); and (b) isolating the hybridizing polynucleotide, which encodes a polypeptide having cellulolytic enhancing activity.

Nucleic Acid Constructs

The present invention also relates to nucleic acid constructs comprising a polynucleotide of the present invention operably linked to one or more (e.g., several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheni-*

*formis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase Ill, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 22 of SEQ ID NO: 2. In another preferred aspect, the signal peptide coding sequence comprises or consists of nucleotides 1 to 66 of SEQ ID NO: 1.

In another preferred aspect, the signal peptide comprises or consists of amino acids 1 to 21 of SEQ ID NO: 4. In another preferred aspect, the signal peptide coding sequence comprises or consists of nucleotides 1 to 63 of SEQ ID NO: 3.

In another preferred aspect, the signal peptide comprises or consists of amino acids 1 to 22 of SEQ ID NO: 6. In another preferred aspect, the signal peptide coding sequence comprises or consists of nucleotides 1 to 66 of SEQ ID NO: 5.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999,

*Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In one aspect, the cell is of the genus *Thermomyces*. In another aspect, the cell is *Thermomyces lanuginosus*. In another aspect, the cell is *Thermomyces lanuginosus* NN044973.

The present invention also relates to methods of producing a polypeptide of the present invention, comprising: (a) cultivating a recombinant host cell of the present invention, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant polynucleotide having at least one mutation in the mature polypeptide coding sequence of SEQ ID NO: 1, SEQ ID NO: 3, or SEQ ID NO: 5, wherein the mutant polynucleotide encodes a polypeptide that comprises or consists of the mature polypeptide of SEQ ID NO: 2, SEQ ID NO: 4, or SEQ ID NO: 6, respectively; and (b) recovering the polypeptide.

The cells are cultivated in a nutrient medium suitable for production of the polypeptide using methods known in the art. For example, the cells may be cultivated by shake flask cultivation, and small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The resulting polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (e.g., several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the polynucleotide encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide having cellulolytic enhancing activity of the present invention under conditions conducive for production of the polypeptide; and (b) recovering the polypeptide.

Removal or Reduction of Cellulolytic Enhancing Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation. The present invention also relates to such double-stranded RNA (dsRNA) molecules, comprising a portion of the mature polypeptide coding sequence of SEQ ID NO: 1, SEQ ID NO: 3, or SEQ ID NO: 5 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially cellulolytic enhancing activity-free product is of particular interest in the production of eukaryotic polypeptides, in particular fungal proteins such as enzymes. The cellulolytic enhancing activity-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity that is produced by a method of the present invention.

Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

The compositions may be prepared in accordance with methods known in the art and may be in the form of a liquid or a dry composition. The compositions may be stabilized in accordance with methods known in the art.

The compositions may be a fermentation broth formulation or a cell composition, as described herein. Consequently, the present invention also relates to fermentation broth formulations and cell compositions comprising a polypeptide having cellulolytic enhancing activity of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or non-viable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The cell-killed whole broth or composition may further comprise one or more enzyme activities such as acetylxylan esterase, alpha-arabinofuranosidase, alpha-galactosidase, alpha-glucuronidase, amylase, arabinanase, arabinofuranosidase, beta-galactosidase, beta-glucosidase, cellobiohydrolase, endoglucanase, endo-beta-1,3(4)-glucanase, ferrulic acid esterase, galactanase, glucoamylase, glucohydrolase, hybrid peroxidases, with combined properties of lignin peroxidases and manganese-dependent peroxidases, laccase, lignin peroxidase, manganese-dependent peroxidases, mannanase, mannan acetyl esterase, mannosidase, pectate lyase, pectin acetyl esterase, pectinase lyase, pectin methyl esterase, polygalacturonase, protease, rhamnogalacturonan lyase, rhamnogalacturonan acetyl esterase, rhamnogalacturonase, xylanase, xylogalacturonosidase, xylogalacturonase, xyloglucanase, and xylosidase.

In some embodiments, the cell-killed whole broth or composition includes cellulolytic enzymes including, but not limited to, (i) endoglucanases (EG) or 1,4-D-glucan-4-glucanohydrolases (EC 3.2.1.4), (ii) exoglucanases, including 1,4-D-glucan glucanohydrolases (also known as cellodextrinases) (EC 3.2.1.74) and 1,4-D-glucan cellobiohydrolases (exo-cellobiohydrolases, CBH) (EC 3.2.1.91), and (iii) beta-glucosidase (BG) or beta-glucoside glucohydrolases (EC 3.2.1.21).

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Uses

The present invention is also directed to the following processes for using the polypeptides having cellulolytic enhancing activity, or compositions thereof.

The present invention also relates to methods for degrading or converting a cellulosic material, comprising: treating the cellulosic material with an enzyme composition in the presence of a polypeptide having cellulolytic enhancing activity of the present invention. In one aspect, the method further comprises recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to methods of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention. In one aspect, the fermenting of the cellulosic material produces a fermentation product. In another aspect, the method further comprises recovering the fermentation product from the fermentation.

The methods of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the methods of the present invention, any pretreatment process known in the art can be used to disrupt plant cell wall components of the cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment: In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005,

*Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having cellulolytic enhancing activity of the present invention. The enzyme components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase).

In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having cellulolytic enhancing activity depend on several factors including, but not limited to, the mixture of cellulolytic and/or hemicellulolytic enzyme components, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having cellulolytic enhancing activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having cellulolytic enhancing activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes NS), CELLIC® CTec2 (Novozymes NS), CELLIC® Ctec3 (Novozymes NS), CELLUCLAST™ (Novozymes NS), NOVOZYM™ 188 (Novozymes NS), CELLUZYME™ (Novozymes NS), CEREFLO™ (Novozymes NS), and ULTRAFLO™ (Novozymes NS), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Rohm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an Acidothermus cellulolyticus endoglucanase (WO 91/05039; WO 93/15186; U.S. Pat. No. 5,275,944; WO 96/02551; U.S. Pat. No. 5,536,655, WO 00/70031, WO 05/093050); Thermobifida fusca endoglucanase III (WO 05/093050); and Thermobifida fusca endoglucanase V (WO 05/093050).

Examples of fungal endoglucanases that can be used in the present invention, include, but are not limited to, a Trichoderma reesei endoglucanase I (Penttila et al., 1986, Gene 45: 253-263, Trichoderma reesei Cel7B endoglucanase I (GENBANK™ accession no. M15665), Trichoderma reesei endoglucanase II (Saloheimo, et al., 1988, Gene 63:11-22), Trichoderma reesei Cel5A endoglucanase II (GENBANK™ accession no. M19373), Trichoderma reesei endoglucanase III (Okada et al., 1988, Appl. Environ. Microbiol. 64: 555-563, GENBANK™ accession no. AB003694), Trichoderma reesei endoglucanase V (Saloheimo et al., 1994, Molecular Microbiology 13: 219-228, GENBANK™ accession no. Z33381), Aspergillus aculeatus endoglucanase (Ooi et al., 1990, Nucleic Acids Research 18: 5884), Aspergillus kawachii endoglucanase (Sakamoto et al., 1995, Current Genetics 27: 435-439), Erwinia carotovara endoglucanase (Saarilahti et al., 1990, Gene 90: 9-14), Fusarium oxysporum endoglucanase (GENBANK™ accession no. L29381), Humicola grisea var. thermoidea endoglucanase (GENBANK™ accession no. AB003107), Melanocarpus albomyces endoglucanase (GENBANK™ accession no. MAL515703), Neurospora crassa endoglucanase (GENBANK™ accession no. XM_324477), Humicola insolens endoglucanase V, Myceliophthora thermophila CBS 117.65 endoglucanase, basidiomycete CBS 495.95 endoglucanase, basidiomycete CBS 494.95 endoglucanase, Thielavia terrestris NRRL 8126 CEL6B endoglucanase, Thielavia terrestris NRRL 8126 CEL6C endoglucanase, Thielavia terrestris NRRL 8126 CEL7C endoglucanase, Thielavia terrestris NRRL 8126 CEL7E endoglucanase, Thielavia terrestris NRRL 8126 CEL7F endoglucanase, Cladorrhinum foecundissimum ATCC 62373 CEL7A endoglucanase, and Trichoderma reesei strain No. VTT-D-80133 endoglucanase (GENBANK™ accession no. M15665).

Examples of cellobiohydrolases useful in the present invention include, but are not limited to, Aspergillus aculeatus cellobiohydrolase II (WO 2011/059740), Chaetomium thermophilum cellobiohydrolase I, Chaetomium thermophilum cellobiohydrolase II, Humicola insolens cellobiohydrolase I, Myceliophthora thermophila cellobiohydrolase II (WO 2009/042871), Thielavia hyrcanie cellobiohydrolase II (WO 2010/141325), Thielavia terrestris cellobiohydrolase II (CEL6A, WO 2006/074435), Trichoderma reesei cellobiohydrolase I, Trichoderma reesei cellobiohydrolase II, and Trichophaea saccata cellobiohydrolase II (WO 2010/057086).

Examples of beta-glucosidases useful in the present invention include, but are not limited to, beta-glucosidases from Aspergillus aculeatus (Kawaguchi et al., 1996, Gene 173: 287-288), Aspergillus fumigatus (WO 2005/047499), Aspergillus niger (Dan et al., 2000, J. Biol. Chem. 275: 4973-4980), Aspergillus oryzae (WO 2002/095014), Penicillium brasilianum IBT 20888 (WO 2007/019442 and WO 2010/088387), Thielavia terrestris (WO 2011/035029), and Trichophaea saccata (WO 2007/019442).

The beta-glucosidase may be a fusion protein. In one aspect, the beta-glucosidase is an Aspergillus oryzae beta-glucosidase variant BG fusion protein (WO 2008/057637) or an Aspergillus oryzae beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, Biochem. J. 280: 309-316, and Henrissat B., and Bairoch A., 1996, Updating the sequence-based classification of glycosyl hydrolases, Biochem. J. 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In one aspect, the GH61 polypeptide having cellulolytic enhancing activity is used in the presence of a soluble activating divalent metal cation according to WO 2008/151043, e.g., manganese sulfate.

In another aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of thebicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisoxazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-6}$ to about 1, about $10^{-6}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-6}$ to about 1 g, about $10^{-6}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes NS), CELLIC® HTec (Novozymes NS), CELLIC® HTec2 (Novozymes NS), VISCOZYME® (Novozymes NS), ULTRAFLO® (Novozymes NS), PULPZYME® HC (Novozymes NS), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number QOCJP9), *Humicola insolens* (WO 2010/014706), *Penicillium* aurantiogriseum (WO 2009/068565), *Talaromyces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol*, 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae.*

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae*; *Clostridium*, such as *C. acetobutylicum, C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus, K. lactis, K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximate $10^5$ to $10^{12}$, preferably from approximate $10^7$ to $10^{10}$, especially approximate $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, World *Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Detergent Compositions

The polypeptides having cellulolytic enhancing activity of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the invention. The detergent additive as well as the detergent composition may comprise one or more (e.g., several) enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™, and CAREZYME™ (Novozymes NS), CLAZINASE™, and PURADAX HA™ (Genencor International Inc.), and KAC-500(B)™ (Kao Corporation).

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include ALCALASE™ SAVINASE™, PRIMASE™, DURALASE™, ESPERASE™, and KANNASE™ (Novozymes NS), MAXATASE™, MAXACAL™, MAXAPEM™, PROPERASE™, PURAFECT™, PURAFECT OXP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta,* 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes NS).

Amylases:

Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes NS), RAPIDASE™ and PURASTAR™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes NS).

The detergent enzyme(s) may be included in a detergent composition by adding separate additives containing one or more (e.g., several) enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more (e.g., several) surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more (e.g., several) polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide of the present invention having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the invention having cellulolytic enhancing activity may also be incorporated in the detergent formulations disclosed in WO 97/07202, which is hereby incorporated by reference.

Signal Peptides

The present invention also relates to an isolated polynucleotide encoding a signal peptide comprising or consisting of amino acids 1 to 22 of SEQ ID NO: 2, amino acids 1 to 21 of SEQ ID NO: 4, or amino acids 1 to 22 of SEQ ID NO: 6. The present invention also relates to nucleic acid constructs comprising a gene encoding a protein, which is operably linked to the signal peptide. The protein is preferably foreign to the signal peptide.

In a preferred aspect, the polynucleotide encoding the signal peptide comprises or consists of nucleotides 1 to 66 of SEQ ID NO: 1, nucleotides 1 to 63 of SEQ ID NO: 3, or nucleotides 1 to 66 of SEQ ID NO: 5.

The present invention also relates to recombinant expression vectors comprising such polynucleotides and recombinant host cells comprising such nucleic acid constructs.

The present invention also relates to methods of producing a protein comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strains

*Thermomyces lanuginosus* strain NN044973 was isolated in 1998 from Yunnan province, China.

Media

PDA medium was composed of 39 grams of potato dextrose agar and deionized water to 1 liter.

YPG medium was composed of 0.4% of yeast extract, 0.1% of $KH_2PO_4$, 0.05% of $MgSO_4.7H_2O$, and 1.5% glucose in deionized water.

Minimal medium plates were composed of 6 g of $NaNO_3$, 0.52 g of KCl, 1.52 g of $KH_2PO_4$, 1 ml of COVE trace elements solution, 20 g of Noble agar, 20 ml of 50% glucose, 2.5 ml of $MgSO_4.7H_2O$, 20 ml of a 0.02% biotin solution, and deionized water to 1 liter.

YPM medium was composed of 1% of yeast extract, 2% of peptone and 2% of maltose in deionized water.

Example 1

*Thermomyces lagnunosis* Genomic DNA Extraction

*Thermomyces lagnunosis* strain NN044973 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by mortar and pestle, to a fine powder, and genomic DNA was isolated using a DNEASY® Plant Maxi Kit (QIAGEN Inc., Valencia, Calif., USA).

Example 2

Genome Sequencing and Assembly

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using SOAPdenovo (Li et al., 2010, *Genome Research* 20(2): 265-72). The assembled sequences were analyzed using standard bioinformatics methods for gene finding and functional prediction. Briefly, geneID (Parra et al., 2000, *Genome Research* 10(4): 511-515) was used for gene prediction. Blastall version 2.2.10 (Altschul et al., 1990, *J. Mol. Biol.* 215 (3): 403-410; National Center for Biotechnology Information (NCBI), Bethesda, Md., USA) and HMMER version 2.1.1 (National Center for Biotechnology Information (NCBI), Bethesda, Md., USA) were used to predict function based on structural homology. The family GH61 polypeptides were identified directly by analysis of the Blast results. The Agene program (Munch and Krogh, 2006, *BMC Bioinformatics* 7: 263) and SignalP program (Nielsen et al., 1997, *Protein Engineering* 10: 1-6) were used to identify starting codons. SignalP was further used to predict the signal peptides.

Example 3

Cloning of the *Thermomyces lanuginosus* GH61(1) Gene from Genomic DNA

Based on a *Thermomyces lanuginosus* GH61 gene sequence as identified in Example 2, oligonucleotide primers, shown below, were designed to amplify the gene from genomic DNA of *Thermomyces lanuginosus*. An IN-FUSION™ CF Dry-down PCR Cloning Kit (Clontech Laboratories, Inc., Mountain View, Calif., USA) was used to clone the fragment directly into the expression vector pPFJO355, without the need for restriction digestion and ligation.

```
Sense primer:
                                        (SEQ ID NO: 7)
5'-ACACAACTGGGGATCC ACC ATGAAGGGCTCCAGCGCTG-3'

Antisense primer:
                                        (SEQ ID NO: 8)
5'-GTCACCCTCTAGATCT CTCAACGCACCATGTACTCGTCTC-3'
```

Lowercase characters of the forward primer represent the coding regions of the gene and lowercase characters of the reverse primer represent the coding region or the flanking region of the gene, while capitalized parts were homologous to the insertion sites of pPFJO355 vector which has been described in US2010306879.

The expression vector pPFJO355 contains the TAKA-amylase promoter derived from *Aspergillus oryzae* and the *Aspergillus niger* glucoamylase terminator elements. Furthermore pPFJO355 has pUC18 derived sequences for selection and propagation in *E. coli*, and a pyrG gene, which encodes an orotidine decarboxylase derived from *Aspergillus nidulans* for selection of a transformant of a pyrG mutant *Aspergillus* strain.

Twenty picomoles of each of the primers above were used in a PCR reaction composed of *Thermomyces lanuginosus* genomic DNA, 10 μl of 5× HF Buffer, 1.5 μl of DMSO, 2 μl of 2.5 mM each of dATP, dTTP, dGTP, and dCTP, and 1 unit of PHUSION™ High-Fidelity DNA Polymerase (Finnzymes Oy, Espoo, Finland) in a final volume of 50 μl. The amplification was performed using a Peltier Thermal Cycler (MJ Research, Inc., Waltham, Mass., USA) programmed for denaturing at 98° C. for 1 minutes; 5 cycles of denaturing at 98° C. for 15 seconds, annealing at 65° C. for 30 seconds, with 1° C. decreasing per cycle and elongation at 72° C. for 60 seconds; and another 25 cycles each at 98° C. for 15 seconds and annealing at 60° C. for 30 seconds; elongation at 72° C. for 60 seconds; final extension at 72° C. for 10 minutes. The heat block then went to a 4° C. soak cycle.

The reaction products were isolated by 1.0% agarose gel electrophoresis using 90 mM Tris-borate and 1 mM EDTA (TBE) buffer where an approximate 900 bp product band was excised from the gel, and purified using an ILLUSTRA™ GFX™ PCR DNA and Gel Band Purification Kit (GE Healthcare, Buckinghamshire, UK) according to the manufacturer's instructions.

Plasmid pPFJO355 was digested with Bam I and Bgl II, isolated by 1.0% agarose gel electrophoresis using TBE buffer, and purified using an ILLUSTRA™ GFX™ PCR DNA and Gel Band Purification Kit according to the manufacturer's instructions.

The gene fragment and the digested vector were ligated together using an IN-FUSION™ Dry-down PCR Cloning kit resulting in pGH61_664 in which transcription of the *Thermomyces lanuginosus* GH61 gene was under the control of a promoter from the gene for *Aspergillus oryzae* alpha-amylase. The cloning operation was according to the manufacturer's instruction. In brief, 30 ng of pPFJO355 digested with Bam I and Bgl II, and 50 ng of the *Thermomyces lanuginosus* GH61 gene purified PCR product were added to a reaction vial and resuspended in a final volume of 5 μl with addition of deionized water. The reaction was incubated at 37° C. for 15 minutes and then 50° C. for 15 minutes. Five μl of the reaction were used to transform *E. coli* TOP10 competent cells (TIANGEN Biotech (Beijing) Co. Ltd., Beijing, China). An *E. coli* transformant containing pGH61_664 was detected by colony PCR and plasmid DNA was prepared using a QIAprep Spin Miniprep Kit (QIAGEN Inc., Valencia, Calif., USA). The inserted GH61 gene was confirmed by a DNA sequencing company (SinoGenoMax, Beijing). *E. coli* TOP10 strain, containing pGH61_664, was deposited with China General Microbiological Culture Collection Center (CGMCC) in Beijing on Feb. 23, 2011, and assigned accession number as CGMCC 4601.

Example 4

Characterization of the Genomic DNA Encoding GH61(1) Polypeptide

The genomic DNA sequence and deduced amino acid sequence of a *Thermomyces lanuginosus* GH61 polypeptide coding sequence are shown in SEQ ID NO: 1 and SEQ ID NO: 2, respectively. The coding sequence is 872 bp including the stop codon which is interrupted by 1 intron of 53 bp (nucleotides 335 to 387). The encoded predicted protein is 272 amino acids. Using the SignalP program (Nielsen et al., 1997, supra), a signal peptide of 22 residues was predicted. The predicted mature protein contains 250 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Thermomyces lanuginosus* genomic DNA encoding a GH61 polypeptide shares 68.0% identity (excluding gaps) to a putative endo-1,4-beta-glucanase from *Aspergillus fumigatus* (UNIPROT: B0XZE1_ASPFC).

Example 5

Expression of *Thermomyces lanuginosus* GH61(1) Gene in *Aspergillus oryzae*

*Aspergillus oryzae* HowB101 (described in WO95/35385 example 1) protoplasts were prepared according to the method of Christensen et al., 1988, *Bio/Technology* 6: 1419-1422. Three μg of pGH61_644 were used to transform *Aspergillus oryzae* HowB101.

The transformation of *Aspergillus oryzae* HowB101 with pGH61_664 yielded about 20 transformants. Four transformants were isolated to individual Minimal medium plates.

Four transformants were inoculated separately into 3 ml of YPM medium in a 24-well plate and incubated at 30° C., 150 rpm. After 3 days incubation, 20 μl of supernatant from each culture were analyzed by SDS-PAGE using a NuPAGE® Novex 4-12% Bis-Tris Gel with 2-(N-morpholino)ethanesulfonic acid (MES) (Invitrogen Corporation, Carlsbad, Calif., USA) according to the manufacturer's instructions. The resulting gel was stained with INSTANT BLUE™ (Expedeon Ltd., Babraham Cambridge, UK). SDS-PAGE profiles of the cultures showed that the majority of the transformants had a band of approximate 40 kDa. The expression strain was designated as O5MMD.

A slant of one transformant was washed with 10 ml of YPM medium and inoculated into a 2 liter flask containing 400 ml of YPM medium to generate broth for characterization of the enzyme. The culture was harvested on day 3 and filtered using a 0.45 μm DURAPORE Membrane (Millipore, Bedford, Mass., USA).

Example 6

Hydrolysis of Pretreated Corn Stover is Enhanced by *Thermomyces Lanuginosus* GH61(1) Polypeptide Having Cellulolytic Enhancing Activity Corn stover was pretreated at the U.S. Department of Energy National Renewable Energy Laboratory (NREL) using 0.048 g sulfuric acid/g dry biomass at 190° C. and 25% w/w dry solids for around 1 minute. The water-insoluble solids in the pretreated corn stover (PCS) contained 54% cellulose. Cellulose was determined by a two-stage sulfuric acid hydrolysis with subsequent analysis of sugars by high performance liquid chromatography (HPLC) using NREL Standard Analytical Procedure #002. Prior to enzymatic hydrolysis, the PCS was washed by water and ground using a Multi Utility Grinder (Inno Concepts Inc., Roswell, Ga., USA) and sieved through a 450 μm screen by AS200 (Retsch, Haman, Germany).

The hydrolysis of pretreated corn stover was conducted using 1.8 ml, 96-deep well plates (Beckman Instruments INC. Fullerton, USA) containing a total reaction mass of 1 g. The hydrolysis was performed with 7.8% total solids of washed pretreated corn stover, equivalent to 54 mg of cellulose per ml, in 5 mM manganese sulfate—20 mM sodium acetate pH 5.0 buffer containing a *Trichoderma reesei* base cellulase mixture (CELLUCLAST® supplemented with *Aspergillus oryzae* beta-glucosidase (recombinantly produced in *Aspergillus oryzae* according to WO 02/095014) available from Novozymes NS, Bagsvaerd, Denmark; the cellulase composition is designated herein in the Examples as "*Trichoderma reesei* cellulase composition") at 2 mg per g of cellulose. *Thermomyces lanuginosus* GH61(1) polypeptide having cellulolytic enhancing activity was separately added to the base cellulase mixture at ranging from 0 to 90% of the concentration of base cellulase mixture. Plates were capped using a Capmat (Beckman Coulter, USA) and incubated at 50° C. and 60° C. for 118 hours with shaking at 150 rpm.

After 118 hours of incubation, 100 µl aliquots were removed and the extent of hydrolysis was assayed by high-performance liquid chromatography (HPLC) using the protocol described below.

For HPLC analysis, samples were filtered with a 0.45 µm MULTISCREEN® 96-well filter plate (Millipore, Bedford, Mass., USA) and filtrates analyzed for sugar content as described below. The sugar concentrations of samples diluted in 5 mM $H_2SO_4$ were measured using a 4.6×250 mm AMINEX® HPX-87H column (Bio-Rad Laboratories, Inc., Hercules, Calif., USA) by elution with 5 mM $H_2SO_4$ at a flow rate of 0.6 ml per minute at 60° C. for 11 minutes, and quantification by integration of the glucose and cellobiose signal from refractive index detection (CHEMSTATION®, AGILENT® 1200 HPLC, Agilent Technologies, Santa Clara, Calif., USA) calibrated by pure sugar samples. The resultant equivalents were used to calculate the percentage of cellulose conversion for each reaction. The extent of each hydrolysis was determined as the fraction of total cellulose converted to cellobiose+glucose, and was not corrected for soluble sugars present in pretreated corn stover liquor.

Measured sugar concentrations were adjusted for the appropriate dilution factor. Glucose and cellobiose were chromatographically separated and integrated and their respective concentrations determined independently. However, to calculate total conversion the glucose and cellobiose values were combined. Fractional hydrolysis is reported as the overall mass conversion to [glucose+cellobiose]/[total cellulose].

The data demonstrated enhancement of hydrolysis by addition of the *Thermomyces lanuginosus* GH61(1) polypeptide having cellulolytic enhancing activity. The addition of the GH61(1) polypeptide at 23%, 37% and 47% (w/w) enhanced hydrolysis by 18.4%, 21.0% and 16.3% glucan conversion in 118 hours of hydrolysis at 50° C., and enhanced hydrolysis by 51.4%, 27.4% and 40.1% glucan conversion in 118 hours of hydrolysis at 60° C.

Example 7

Cloning of the *Thermomyces lanuginosus* GH61(2) Gene from Genomic DNA

Based on a *Thermomyces lanuginosus* GH61 gene sequence as identified in Example 2, oligonucleotide primers, shown below, were designed to amplify the gene from genomic DNA of *Thermomyces lanuginosus* prepared in Example 1. An IN-FUSION™ CF Dry-down PCR Cloning Kit (Clontech Laboratories, Inc., Mountain View, Calif., USA) was used to clone the fragment directly into the expression vector pPFJO355, without the need for restriction digestion and ligation.

Sense primer:
(SEQ ID NO: 9)
5'-ACACAACTGGGGATCC ACC ATGGCATTCTCTACGGTTACAGTTTT TGTTAC-3'

Antisense primer:
(SEQ ID NO: 10)
5'-GTCACCCTCTAGATCT AATGAGAGAGCATATCCATAACCGCAT-3'

Lowercase characters of the forward primer represent the coding regions of the gene and lowercase characters of the reverse primer represent the coding region or the flanking region of the gene, while capitalized parts were homologous to the insertion sites of pPFJO355 vector which has been described in US2010306879.

The expression vector pPFJO355 contains the TAKA-amylase promoter derived from *Aspergillus oryzae* and the *Aspergillus niger* glucoamylase terminator elements. Furthermore pPFJO355 has pUC18 derived sequences for selection and propagation in *E. coli*, and a pyrG gene, which encodes an orotidine decarboxylase derived from *Aspergillus nidulans* for selection of a transformant of a pyrG mutant *Aspergillus* strain.

Twenty picomoles of each of the primers above were used in a PCR reaction composed of *Thermomyces lanuginosus* genomic DNA, 10 µl of 5× HF Buffer, 1.5 µl of DMSO, 2 µl of 2.5 mM each of dATP, dTTP, dGTP, and dCTP, and 1 unit of PHUSION™ High-Fidelity DNA Polymerase (Finnzymes Oy, Espoo, Finland) in a final volume of 50 µl. The amplification was performed using a Peltier Thermal Cycler (MJ Research, Inc., Waltham, Mass., USA) programmed for denaturing at 98° C. for 1 minute; 5 cycles of denaturing at 98° C. for 15 seconds, annealing at 65° C. for 30 seconds, with 1° C. decreasing per cycle and elongation at 72° C. for 60 seconds; and another 25 cycles each at 98° C. for 15 seconds and annealing at 60° C. for 30 seconds; elongation at 72° C. for 60 seconds; and a final extension at 72° C. for 10 minutes. The heat block then went to a 4° C. soak cycle.

The reaction products were isolated by 1.0% agarose gel electrophoresis using 90 mM Tris-borate and 1 mM EDTA (TBE) buffer where an approximate 1.0 kb product band was excised from the gel, and purified using an ILLUSTRA™ GFX™ PCR DNA and Gel Band Purification Kit (GE Healthcare, Buckinghamshire, UK) according to the manufacturer's instructions.

Plasmid pPFJO355 was digested with Bam I and Bgl II, isolated by 1.0% agarose gel electrophoresis using TBE buffer, and purified using an ILLUSTRA™ GFX™ PCR DNA and Gel Band Purification Kit according to the manufacturer's instructions.

The gene fragment and the digested vector were ligated together using an IN-FUSION™ Dry-down PCR Cloning kit resulting in pGH61_1590 in which transcription of the *Thermomyces lanuginosus* GH61 gene was under the control of a promoter from the gene for *Aspergillus oryzae* alpha-amylase. The cloning operation was according to the manufacturer's instruction. In brief, 30 ng of pPFJO355 digested with Bam I and Bgl II, and 50 ng of the *Thermomyces lanuginosus* GH61 gene purified PCR product were added to a reaction vial and the reaction powder was resuspended in a final volume of 5 µl with addition of deionized water. The reaction was incubated at 37° C. for 15 minutes and then 50° C. for 15 minutes. Five µl of the reaction were used to transform *E. coli* TOP10 competent cells (TIANGEN Biotech (Beijing) Co.

Ltd., Beijing, China). An *E. coli* transformant containing pGH61_1590 was detected by colony PCR and plasmid DNA was prepared using a QIAprep Spin Miniprep Kit (QIAGEN Inc., Valencia, Calif., USA). The inserted GH61 gene was confirmed by a DNA sequencing company (SinoGenoMax, Beijing). *E. coli* TOP10 strain, containing pGH61_1590, was deposited with China General Microbiological Culture Collection Center (CGMCC) in Beijing on Feb. 23, 2011, and assigned accession number as CGMCC 4602.

Example 8

Characterization of the Genomic DNA Encoding GH61(2) Polypeptide

The genomic DNA sequence and deduced amino acid sequence of a *Thermomyces lanuginosus* GH61 polypeptide coding sequence are shown in SEQ ID NO: 3 and SEQ ID NO: 4, respectively. The coding sequence is 1039 bp including the stop codon which is interrupted by 1 intron of 55 bp (nucleotides 111 to 165). The encoded predicted protein is 327 amino acids. Using the SignalP program (Nielsen et al., 1997, supra), a signal peptide of 21 residues was predicted. The predicted mature protein contains 306 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Thermomyces lanuginosus* genomic DNA encoding a GH61 polypeptide shares 49.2% identity (excluding gaps) to a *Thermoascus aurantiacus* GH61 B protein (WO 2010065830).

Example 9

Expression of *Thermomyces lanuginosus* GH61(2) Gene in *Aspergillus oryzae*

*Aspergillus oryzae* HowB101 (described in WO95/35385 example 1) protoplasts were prepared according to the method of Christensen et al., 1988, *Bio/Technology* 6: 1419-1422. Three μg of pGH61_1590 were used to transform *Aspergillus oryzae* HowB101.

The transformation of *Aspergillus oryzae* HowB101 with pGH61_1590 yielded about 20 transformants. Four transformants were isolated to individual Minimal medium plates.

Four transformants were inoculated separately into 3 ml of YPM medium in a 24-well plate and incubated at 30° C., 150 rpm. After 3 days incubation, 20 μl of supernatant from each culture were analyzed by SDS-PAGE using a NuPAGE® Novex 4-12% Bis-Tris Gel with 2-(N-morpholino)ethanesulfonic acid (MES) (Invitrogen Corporation, Carlsbad, Calif., USA) according to the manufacturer's instructions. The resulting gel was stained with INSTANT BLUE™ (Expedeon Ltd., Babraham Cambridge, UK). SDS-PAGE profiles of the cultures showed that the majority of the transformants had a smear of approximate 60 kDa. The expression strain was designated as O5MME.

A slant of one transformant was washed with 10 ml of YPM medium and inoculated into a 2 liter flask containing 400 ml of YPM medium to generate broth for characterization of the enzyme. The culture was harvested on day 3 and filtered using a 0.45 μm DURAPORE Membrane (Millipore, Bedford, Mass., USA).

Example 10

Purification of Recombinant *Thermomyces lanuginosus* GH61(2) from *Aspergillus oryzae*

3200 ml supernatant of the recombinant transformant prepared as described in Example 9 was precipitated with ammonium sulfate (80% saturation) and re-dissolved in 50 ml of 20 mM Tris-HCl buffer, pH6.5, then dialyzed against the same buffer and filtered through a 0.45 mm filter, the final volume was 110 ml. The solution was applied to a 40 ml Q SEPHAROSE® Fast Flow column (GE Healthcare, Buckinghamshire, UK) equilibrated in 20 mM Tris-HCl buffer, pH6.5, and the proteins was eluted with a linear NaCl gradient (0-0.25M). Fractions were evaluated by SDS-PAGE (NP0336BOX, NuPAGE® Novex 4-12% Bis-Tris GEL 1.5 mM15 W). Fractions containing a band of approximate 35 kDa were pooled. Then the pooled solution was concentrated by ultrafiltration.

Example 11

Hydrolysis of Pretreated Corn Stover is Enhanced by *Thermomyces lanuginosus* GH61(2) Polypeptide Having Cellulolytic Enhancing Activity The hydrolysis of dilute acid pretreated corn stover (PCS) was conducted using 1.8 mL, 96-deep well plates (Beckman Instruments INC. Fullerton, USA) containing a total reaction mass of 1 g. The hydrolysis was performed with 7.2% total solids of washed, pretreated corn stover, equivalent to 50 mg of cellulose per ml, in 5 mM manganese sulfate—20 mM sodium acetate pH 5.0 buffer containing a *Trichoderma reesei* cellulase composition (CELLUCLAST® supplemented with *Aspergillus oryzae* beta-glucosidase (recombinantly produced in *Aspergillus oryzae* according to WO 02/095014) available from Novozymes NS, Bagsvaerd, Denmark; the cellulase composition is designated herein in the Examples as "*Trichoderma reesei* cellulase composition") at 2 mg per g of cellulose. *Thermomyces lanuginosus* GH61(2) polypeptide having cellulolytic enhancing activity was added at concentrations of 23% (w/w) of total protein. Plates were capped using a Capmat (Beckman Coulter, USA) and incubated at 60° C. for 44 hours with shaking at 150 rpm. All experiments were performed in triplicate.

After 44 hours of incubation, 100 μl aliquots were removed and the extent of hydrolysis was assayed by high-performance liquid chromatography (HPLC) using the protocol described below.

For HPLC analysis, samples were filtered with a 0.45 μm MULTISCREEN® 96-well filter plate (Millipore, Bedford, Mass., USA) and filtrates analyzed for sugar content as described below. The sugar concentrations of samples diluted in 5 mM $H_2SO_4$ were measured using a 4.6×250 mm AMINEX® HPX-87H column (Bio-Rad Laboratories, Inc., Hercules, Calif., USA) by elution with 5 mM $H_2SO_4$ at a flow rate of 0.6 ml per minute at 60° C. for 11 minutes, and quantification by integration of the glucose and cellobiose signal from refractive index detection (CHEMSTATION®, AGILENT® 1200 HPLC, Agilent Technologies, Santa Clara, Calif., USA) calibrated by pure sugar samples. The resultant equivalents were used to calculate the percentage of cellulose conversion for each reaction. The extent of each hydrolysis was determined as the fraction of total cellulose converted to cellobiose+glucose, and was not corrected for soluble sugars present in pretreated corn stover liquor.

Measured sugar concentrations were adjusted for the appropriate dilution factor. Glucose and cellobiose were chromatographically separated and integrated and their respective concentrations determined independently. However, to calculate total conversion the glucose and cellobiose values were combined. Fractional hydrolysis is reported as the overall mass conversion to [glucose+cellobiose]/[total cellulose]. Triplicate data points were averaged.

The data demonstrated enhancement of hydrolysis by addition of the *Thermomyces lanuginosus* GH61(2) polypeptide having cellulolytic enhancing activity. Addition of the GH61 polypeptide at 23% (w/w) enhanced hydrolysis by 3.99%, from 6.51% to 6.77% glucan conversion in 44 hours of hydrolysis.

Example 12

Cloning of the *Thermomyces lanuginosus* GH61(3) Gene from Genomic DNA

Based on a *Thermomyces lanuginosus* GH61 gene sequence as identified in Example 2, oligonucleotide primers, shown below, were designed to amplify the gene from genomic DNA of *Thermomyces lanuginosus* prepared in Example 1. An IN-FUSION™ CF Dry-down PCR Cloning Kit (Clontech Laboratories, Inc., Mountain View, Calif., USA) was used to clone the fragment directly into the expression vector pPFJO355, without the need for restriction digestion and ligation.

```
Sense primer:
                                          (SEQ ID NO: 11)
5'-ACACAACTGGGGATCC ACC ATGAAAGGCTCCACCACTGCG-3'

Antisense primer:
                                          (SEQ ID NO: 12)
5'-GTCACCCTCTAGATCT CAGCGGTAGCAAGCATTCGACT-3'
```

Lowercase characters of the forward primer represent the coding regions of the gene and lowercase characters of the reverse primer represent the coding region or the flanking region of the gene, while capitalized parts were homologous to the insertion sites of pPFJO355 vector which has been described in US2010306879.

The expression vector pPFJO355 contains the TAKA-amylase promoter derived from *Aspergillus oryzae* and the *Aspergillus niger* glucoamylase terminator elements. Furthermore pPFJO355 has pUC18 derived sequences for selection and propagation in *E. coli*, and a pyrG gene, which encodes an orotidine decarboxylase derived from *Aspergillus nidulans* for selection of a transformant of a pyrG mutant *Aspergillus* strain.

Twenty picomoles of each of the primers above were used in a PCR reaction composed of *Thermomyces lanuginosus* genomic DNA, 10 μl of 5× HF Buffer, 1.5 μl of DMSO, 2 μl of 2.5 mM each of dATP, dTTP, dGTP, and dCTP, and 1 unit of PHUSION™ High-Fidelity DNA Polymerase (Finnzymes Oy, Espoo, Finland) in a final volume of 50 μl. The amplification was performed using a Peltier Thermal Cycler (MJ Research, Inc., Waltham, Mass., USA) programmed for denaturing at 98° C. for 1 minutes; 5 cycles of denaturing at 98° C. for 15 seconds, annealing at 65° C. for 30 seconds, with 1° C. decreasing per cycle and elongation at 72° C. for 60 seconds; and another 25 cycles each at 98° C. for 15 seconds and annealing at 60° C. for 30 seconds; elongation at 72° C. for 60 seconds; final extension at 72° C. for 10 minutes. The heat block then went to a 4° C. soak cycle.

The reaction products were isolated by 1.0% agarose gel electrophoresis using 90 mM Tris-borate and 1 mM EDTA (TBE) buffer where an approximate 900 bp product band was excised from the gel, and purified using an ILLUSTRA™ GFX™ PCR DNA and Gel Band Purification Kit (GE Healthcare, Buckinghamshire, UK) according to the manufacturer's instructions.

Plasmid pPFJO355 was digested with Bam I and Bgl II, isolated by 1.0% agarose gel electrophoresis using TBE buffer, and purified using an ILLUSTRA™ GFX™ PCR DNA and Gel Band Purification Kit according to the manufacturer's instructions.

The gene fragment and the digested vector were ligated together using an IN-FUSION™ Dry-down PCR Cloning kit resulting in pGH61_4950 in which transcription of the *Thermomyces lanuginosus* GH61 gene was under the control of a promoter from the gene for *Aspergillus oryzae* alpha-amylase. The cloning operation was according to the manufacturer's instruction. In brief, 30 ng of pPFJO355 digested with Bam I and Bgl II, and 50 ng of the *Thermomyces lanuginosus* GH61 gene purified PCR product were added to a reaction vial and resuspended in a final volume of 5 μl with addition of deionized water. The reaction was incubated at 37° C. for 15 minutes and then 50° C. for 15 minutes. Five μl of the reaction were used to transform *E. coli* TOP10 competent cells (TIANGEN Biotech (Beijing) Co. Ltd., Beijing, China). An *E. coli* transformant containing pGH61_4950 was detected by colony PCR and plasmid DNA was prepared using a QIAprep Spin Miniprep Kit (QIAGEN Inc., Valencia, Calif., USA). The inserted GH61 gene was confirmed by a DNA sequencing company (SinoGenoMax, Beijing). *E. coli* TOP10 strain, containing pGH61_4950, was deposited with China General Microbiological Culture Collection Center (CGMCC) in Beijing, China on Feb. 23, 2011, and assigned accession number as CGMCC 4600.

Example 13

Characterization of the Genomic DNA Encoding GH61(3) Polypeptide

The genomic DNA sequence and deduced amino acid sequence of a *Thermomyces lanuginosus* GH61 polypeptide coding sequence are shown in SEQ ID NO: 5 and SEQ ID NO: 6, respectively. The coding sequence is 881 bp including the stop codon which is interrupted by 1 intron of 56 bp (nucleotides 335 to 390). The encoded predicted protein is 274 amino acids. Using the SignalP program (Nielsen et al., 1997, supra), a signal peptide of 22 residues was predicted. The predicted mature protein contains 252 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Thermomyces lanuginosus* genomic DNA encoding a GH61 polypeptide shares 68.40% identity (excluding gaps) to a putative endo-1,4-beta-glucanase from *Aspergillus fumigatus* (UNIPROT: B0XZE1_ASPFC).

Example 14

Expression of *Thermomyces lanuginosus* GH61(3) Gene in *Aspergillus oryzae*

*Aspergillus oryzae* HowB101 (described in WO95/35385 example 1) protoplasts were prepared according to the method of Christensen et al., 1988, *Bio/Technology* 6: 1419-1422. Three μg of pGH61_4950 were used to transform *Aspergillus oryzae* HowB101.

The transformation of *Aspergillus oryzae* HowB101 with pGH61_4950 yielded about 20 transformants. Four transformants were isolated to individual Minimal medium plates.

Four transformants were inoculated separately into 3 ml of YPM medium in a 24-well plate and incubated at 30° C., 150 rpm. After 3 days incubation, 20 μl of supernatant from each culture were analyzed by SDS-PAGE using a NuPAGE® Novex 4-12% Bis-Tris Gel with 2-(N-morpholino)ethanesulfonic acid (MES) (Invitrogen Corporation, Carlsbad, Calif., USA) according to the manufacturer's instructions. The resulting gel was stained with INSTANT BLUE™ (Expedeon Ltd., Babraham Cambridge, UK). SDS-PAGE profiles of the cultures showed that the majority of the transformants had a band of approximate 45 kDa. The expression strain was designated as O5MMC.

A slant of one transformant was washed with 10 ml of YPM medium and inoculated into a 2 liter flask containing 400 ml of YPM medium to generate broth for characterization of the enzyme. The culture was harvested on day 3 and filtered using a 0.45 μm DURAPORE Membrane (Millipore, Bedford, Mass., USA).

Example 15

Hydrolysis of Pretreated Corn Stover is Enhanced by *Thermomyces lanuginosus* GH61(3) Polypeptide Having Cellulolytic Enhancing Activity Corn stover was pretreated at the U.S. Department of Energy National Renewable Energy Laboratory (NREL) using 0.048 g sulfuric acid/g dry biomass at 190° C. and 25% w/w dry solids for around 1 minute. The water-insoluble solids in the pretreated corn stover (PCS) contained 54% cellulose. Cellulose was determined by a two-stage sulfuric acid hydrolysis with subsequent analysis of sugars by high performance liquid chromatography (HPLC) using NREL Standard Analytical Procedure #002. Prior to enzymatic hydrolysis, the PCS was washed by water and ground using a Multi Utility Grinder (Inno Concepts Inc., Roswell, Ga., USA) and sieved through a 450 μm screen by AS200 (Retsch, Haman, Germany).

The hydrolysis of pretreated corn stover was conducted using 1.8 ml, 96-deep well plates (Beckman Instruments INC. Fullerton, USA) containing a total reaction mass of 1 g. The hydrolysis was performed with 7.8% total solids of washed pretreated corn stover, equivalent to 54 mg of cellulose per ml, in 5 mM manganese sulfate—20 mM sodium acetate pH 5.0 buffer containing a *Trichoderma reesei* base cellulase mixture (CELLUCLAST® supplemented with *Aspergillus oryzae* beta-glucosidase (recombinantly produced in *Aspergillus oryzae* according to WO 02/095014) available from Novozymes NS, Bagsvaerd, Denmark; the cellulase composition is designated herein in the Examples as "*Trichoderma reesei* cellulase composition") at 2 mg per g of cellulose. *Thermomyces lanuginosus* GH61(3) polypeptide having cellulolytic enhancing activity was separately added to the base cellulase mixture at ranging from 0 to 90% of the concentration of base cellulase mixture. Plates were capped using a Capmat (Beckman Coulter, USA) and incubated at 50° C. and 60° C. for 118 hours with shaking at 150 rpm.

After 118 hours of incubation, 100 μl aliquots were removed and the extent of hydrolysis was assayed by high-performance liquid chromatography (HPLC) using the protocol described below.

For HPLC analysis, samples were filtered with a 0.45 μm MULTISCREEN® 96-well filter plate (Millipore, Bedford, Mass., USA) and filtrates analyzed for sugar content as described below. The sugar concentrations of samples diluted in 5 mM $H_2SO_4$ were measured using a 4.6×250 mm AMINEX® HPX-87H column (Bio-Rad Laboratories, Inc., Hercules, Calif., USA) by elution with 5 mM $H_2SO_4$ at a flow rate of 0.6 ml per minute at 60° C. for 11 minutes, and quantification by integration of the glucose and cellobiose signal from refractive index detection (CHEMSTATION®, AGILENT® 1200 HPLC, Agilent Technologies, Santa Clara, Calif., USA) calibrated by pure sugar samples. The resultant equivalents were used to calculate the percentage of cellulose conversion for each reaction. The extent of each hydrolysis was determined as the fraction of total cellulose converted to cellobiose+glucose, and was not corrected for soluble sugars present in pretreated corn stover liquor.

Measured sugar concentrations were adjusted for the appropriate dilution factor. Glucose and cellobiose were chromatographically separated and integrated and their respective concentrations determined independently. However, to calculate total conversion the glucose and cellobiose values were combined. Fractional hydrolysis is reported as the overall mass conversion to [glucose+cellobiose]/[total cellulose]. Triplicate data points were averaged.

The data demonstrated enhancement of hydrolysis by addition of the *Thermomyces lanuginosus* GH61(3) polypeptide having cellulolytic enhancing activity. The addition of the GH61(3) polypeptide at 23%, 37% and 47% (w/w) enhanced hydrolysis by 24.0%, 25.8% and 26.7% glucan conversion in 118 hours of hydrolysis at 50° C., and enhanced hydrolysis by 82.7%, 13.3% and 0.0% glucan conversion in 118 hours of hydrolysis at 60° C.

DEPOSIT OF BIOLOGICAL MATERIAL

The following biological material has been deposited under the terms of the Budapest Treaty with China General Microbiological Culture Collection Center (CGMCC), NO. 1 West Beichen Road, Chaoyang District, Beijing 100101, China, and given the following accession number:

| Deposit | Accession Number | Date of Deposit |
| --- | --- | --- |
| *E. coli* (1) | CGMCC 4601 | Feb. 23, 2011 |
| *E. coli* (2) | CGMCC 4602 | Feb. 23, 2011 |
| *E. coli* (3) | CGMCC 4600 | Feb. 23, 2011 |

The strains have been deposited under conditions that assure that access to the cultures will be available during the pendency of this patent application to one determined by foreign patent laws to be entitled thereto. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The present invention is further described by the following numbered paragraphs:

[1] An isolated polypeptide having cellulolytic enhancing activity, selected from the group consisting of:

(a) a polypeptide having at least 70% sequence identity to the mature polypeptide of SEQ ID NO: 2, or at least 60% sequence identity to the mature polypeptide of SEQ ID NO: 4, or at least 70% sequence identity to the mature polypeptide of SEQ ID NO: 6;

(b) a polypeptide encoded by a polynucleotide that hybridizes under at least high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii);

(c) a polypeptide encoded by a polynucleotide having at least 70% sequence identity to the mature polypeptide coding sequence of SEQ ID NO: 1 or the cDNA sequence thereof, or at least 60% sequence identity to the mature polypeptide coding sequence of SEQ ID NO: 3 or the cDNA sequence thereof, or at least 70% sequence identity to the mature polypeptide coding sequence of SEQ ID NO: 5 or the cDNA sequence thereof;

(d) a variant of the mature polypeptide of SEQ ID NO: 2, SEQ ID NO: 4 or SEQ ID NO: 6 comprising a substitution, deletion, and/or insertion of one or more (e.g., several) amino acids; and (e) a fragment of the polypeptide of (a), (b), (c), or (d) that has cellulolytic enhancing activity.

[2] The polypeptide of paragraph 1, having at least 75% identity, preferably at least 80%, at least 81%, at least 82%, at least 83%, at least 84%, at least 85%, at least 86%, at least 87%, at least 88%, at least 89% or at least 90% sequence identity to the mature polypeptide of SEQ ID NO: 2 or SEQ ID NO: 6.

[3] The polypeptide of paragraph 2, having at least 91%, at least 92%, at least 93%, at least 94%, or at least 95% sequence identity to the mature polypeptide of SEQ ID NO: 2 or SEQ ID NO: 6.

[4] The polypeptide of paragraph 3, having at least 96%, at least 97%, at least 98%, at least 99%, or 100% sequence identity to the mature polypeptide of SEQ ID NO: 2 or SEQ ID NO: 6.

[5] The polypeptide of paragraph 1, having at least 65% identity, more preferably at least 70% identity, most preferably at least 75% sequence identity to the mature polypeptide of SEQ ID NO: 4.

[6] The polypeptide of paragraph 5, having at least 80%, at least 81%, at least 82%, at least 83%, at least 84%, at least 85%, at least 86%, at least 87%, at least 88%, at least 89% or at least 90% sequence identity to the mature polypeptide of SEQ ID NO: 4.

[7] The polypeptide of paragraph 6, having at least 91%, at least 92%, at least 93%, at least 94%, or at least 95% sequence identity to the mature polypeptide of SEQ ID NO: 4.

[8] The polypeptide of paragraph 7, having at least 95% sequence identity to the mature polypeptide of SEQ ID NO: 4.

[9] The polypeptide of paragraph 8, having at least 96%, at least 97%, at least 98%, at least 99%, or 100% sequence identity to the mature polypeptide of SEQ ID NO: 4.

[10] The polypeptide of paragraph 1, comprising or consisting of the amino acid sequence of SEQ ID NO: 2, SEQ ID NO: 4, or SEQ ID NO: 6; or a fragment thereof having cellulolytic enhancing activity.

[11] The polypeptide of paragraph 10, comprising or consisting of the amino acid sequence of SEQ ID NO: 2, SEQ ID NO: 4, or SEQ ID NO: 6.

[12] The polypeptide of paragraph 10, comprising or consisting of the mature polypeptide of SEQ ID NO: 2, SEQ ID NO: 4, or SEQ ID NO: 6.

[13] The polypeptide of paragraph 1, which is encoded by a polynucleotide that hybridizes under at least medium stringency conditions, preferably at least medium-high, at least high, or at least very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii).

[14] The polypeptide of paragraph 13, which is encoded by a polynucleotide that hybridizes under at least medium-high, at least high, or at least very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii).

[15] The polypeptide of paragraph 1, which is encoded by a polynucleotide having at least 70% sequence identity, preferably at least 75% sequence identity, more preferably at least 80%, at least 81%, at least 82%, at least 83%, at least 84%, or at least 85% sequence identity to the mature polypeptide coding sequence of SEQ ID NO: 1 or SEQ ID NO: 5.

[16] The polypeptide of paragraph 15, which is encoded by a polynucleotide having at least 86%, at least 87%, at least 88%, at least 89%, at least 90%, at least 91%, at least 92%, at least 93%, at least 94%, or at least 95% sequence identity to the mature polypeptide coding sequence of SEQ ID NO: 1 or SEQ ID NO: 5.

[17] The polypeptide of paragraph 16, which is encoded by a polynucleotide having at least 96%, at least 97%, at least 98%, at least 99%, or 100% sequence identity to the mature polypeptide coding sequence of SEQ ID NO: 1 or SEQ ID NO: 5.

[18] The polypeptide of paragraph 1, which is encoded by a polynucleotide having at least 65% sequence identity, more preferably at least 70% sequence identity, most preferably at least 75% sequence identity to the mature polypeptide coding sequence of SEQ ID NO: 3.

[19] The polypeptide of paragraph 18, which is encoded by a polynucleotide having at least 80%, at least 81%, at least 82%, at least 83%, at least 84%, or at least 85% sequence identity to the mature polypeptide coding sequence of SEQ ID NO: 3.

[20] The polypeptide of paragraph 19, which is encoded by a polynucleotide having at least 86%, at least 87%, at least 88%, at least 89%, or at least 90% sequence identity to the mature polypeptide coding sequence of SEQ ID NO: 3.

[21] The polypeptide of paragraph 20, which is encoded by a polynucleotide having at least 91%, at least 92%, at least 93%, at least 94%, or at least 95% sequence identity to the mature polypeptide coding sequence of SEQ ID NO: 3.

[22] The polypeptide of paragraph 21, which is encoded by a polynucleotide having at least 96%, at least 97%, at least 98%, at least 99%, or 100% sequence identity to the mature polypeptide coding sequence of SEQ ID NO: 3.

[23] The polypeptide of paragraph 1, which is encoded by a polynucleotide comprising or consisting of the polynucleotide of SEQ ID NO: 1, SEQ ID NO: 3, or SEQ ID NO: 5; or a subsequence thereof encoding a fragment having cellulolytic enhancing activity.

[24] The polypeptide of paragraph 23, which is encoded by a polynucleotide comprising or consisting of the polynucleotide of SEQ ID NO: 1, SEQ ID NO: 3, or SEQ ID NO: 5.

[25] The polypeptide of paragraph 23, which is encoded by a polynucleotide comprising or consisting of the mature polypeptide coding sequence of SEQ ID NO: 1, SEQ ID NO: 3, or SEQ ID NO: 5.

[26] The polypeptide of paragraph 1, wherein the polypeptide is a variant of the mature polypeptide of SEQ ID NO: 2, SEQ ID NO: 4, or SEQ ID NO: 6 comprising a substitution, deletion, and/or insertion of one or more (e.g., several) amino acids.

[27] The polypeptide of paragraph 1, which is encoded by the polynucleotide contained in plasmid pGH61_664 which is contained in *E. coli* CGMCC 4601, plasmid pGH61_1590 which is contained in *E. coli* CGMCC 4602, or plasmid pGH61_4950 which is contained in *E. coli* CGMCC 4600.

[28] The polypeptide of any of paragraphs 1-27, wherein the mature polypeptide is amino acids 23 to 272 of SEQ ID NO: 2, amino acids 22 to 327 of SEQ ID NO: 4, or amino acids 23 to 274 of SEQ ID NO: 6.

[29] The polypeptide of any of paragraphs 1-28, wherein the mature polypeptide coding sequence is nucleotides 67 to 869 of SEQ ID NO: 1, nucleotides 64 to 1036 of SEQ ID NO: 3, or nucleotides 67 to 878 of SEQ ID NO: 5 or the cDNA sequence thereof.

[30] An isolated polynucleotide encoding the polypeptide of any of paragraphs 1-29.

[31] The isolated polynucleotide of paragraph 30, comprising at least one mutation in the mature polypeptide coding sequence of SEQ ID NO: 1, SEQ ID NO: 3, or SEQ ID NO: 5, in which the mutant polynucleotide encodes the mature polypeptide of SEQ ID NO: 2, SEQ ID NO: 4, or SEQ ID NO: 6, respectively.

[32] A nucleic acid construct comprising the polynucleotide of paragraph 30 or 31 operably linked to one or more (e.g., several) control sequences that direct the production of the polypeptide in an expression host.

[33] A recombinant expression vector comprising the nucleic acid construct of paragraph 32.

[34] A recombinant host cell comprising the nucleic acid construct of paragraph 32.

[35] A method of producing the polypeptide of any of paragraphs 1-29, comprising:
(a) cultivating a cell, which in its wild-type form produces the polypeptide, under conditions conducive for production of the polypeptide; and
(b) recovering the polypeptide.

[36] A method of producing the polypeptide of any of paragraphs 1-29, comprising:
(a) cultivating a host cell comprising a nucleic acid construct comprising a polynucleotide encoding the polypeptide under conditions conducive for production of the polypeptide; and
(b) recovering the polypeptide.

[37] A method of producing a mutant of a parent cell, comprising disrupting or deleting a polynucleotide encoding the polypeptide, or a portion thereof, of any of paragraphs 1-29, which results in the mutant producing less of the polypeptide than the parent cell.

[38] A mutant cell produced by the method of paragraph 37.

[39] The mutant cell of paragraph 38, further comprising a gene encoding a native or heterologous protein.

[40] A method of producing a protein, comprising:
(a) cultivating the mutant cell of paragraph 39 under conditions conducive for production of the protein; and
(b) recovering the protein.

[41] The isolated polynucleotide of paragraph 30 or 31, obtained by (a) hybridizing a population of DNA under at least medium, at least medium-high, at least high, or at least very high stringency conditions with (i) the mature polypeptide coding sequence of SEQ ID NO: 1, SEQ ID NO: 3, or SEQ ID NO:5, (ii) the cDNA sequence contained in the mature polypeptide coding sequence of SEQ ID NO: 1, SEQ ID NO: 3, or SEQ ID NO:5, or (iii) a full-length complementary strand of (i) or (ii); and (b) isolating the hybridizing polynucleotide, which encodes a polypeptide having cellulolytic enhancing activity.

[42] The isolated polynucleotide of paragraph 41, obtained by (a) hybridizing a population of DNA under at least medium-high, at least high, or at least very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii); and (b) isolating the hybridizing polynucleotide, which encodes a polypeptide having cellulolytic enhancing activity.

[43] The isolated polynucleotide of paragraph 41 or 42, wherein the mature polypeptide coding sequence is nucleotides 67 to 869 of SEQ ID NO: 1, nucleotides 64 to 1036 of SEQ ID NO: 3, or nucleotides 67 to 878 of SEQ ID NO: 5.

[44] A method of producing a polynucleotide comprising a mutant polynucleotide encoding a polypeptide having cellulolytic enhancing activity, comprising:
(a) introducing at least one mutation into the mature polypeptide coding sequence of SEQ ID NO: 1, SEQ ID NO: 3, or SEQ ID NO: 5, wherein the mutant polynucleotide encodes a polypeptide comprising or consisting of the mature polypeptide of SEQ ID NO: 2, SEQ ID NO: 4, or SEQ ID NO: 6; and
(b) recovering the polynucleotide comprising the mutant nucleotide sequence.

[45] A mutant polynucleotide produced by the method of paragraph 44.

[46] A method of producing a polypeptide, comprising:
(a) cultivating a cell comprising the mutant polynucleotide of paragraph 45 encoding the polypeptide under conditions conducive for production of the polypeptide; and
(b) recovering the polypeptide.

[47] A method of producing the polypeptide of any of paragraphs 1-29, comprising:
(a) cultivating a transgenic plant or a plant cell comprising a polynucleotide encoding the polypeptide under conditions conducive for production of the polypeptide; and
(b) recovering the polypeptide.

[48] A transgenic plant, plant part or plant cell transformed with a polynucleotide encoding the polypeptide of any of paragraphs 1-29.

[49] A double-stranded RNA (dsRNA) molecule comprising a subsequence of the polynucleotide of paragraph 30 or 31, wherein optionally the dsRNA is an siRNA or an miRNA molecule.

[50] The double-stranded RNA (dsRNA) molecule of paragraph 49, which is about 15, 16, 17, 18, 19, 20, 21, 22, 23, 24, 25 or more duplex nucleotides in length.

[51] A method of inhibiting the expression of a polypeptide having cellulolytic enhancing activity in a cell, comprising administering to the cell or expressing in the cell a double-stranded RNA (dsRNA) molecule, wherein the dsRNA comprises a subsequence of the polynucleotide of paragraph 30 or 31.

[52] The method of paragraph 51, wherein the dsRNA is about 15, 16, 17, 18, 19, 20, 21, 22, 23, 24, 25 or more duplex nucleotides in length.

[53] An isolated polynucleotide encoding a signal peptide comprising or consisting of amino acids 1 to 22 of SEQ ID NO: 2, amino acids 1 to 21 of SEQ ID NO: 4, or amino acids 1 to 22 of SEQ ID NO: 6.

[54] A nucleic acid construct comprising a gene encoding a protein operably linked to the polynucleotide of paragraph 53, wherein the gene is foreign to the polynucleotide.

[55] A recombinant expression vector comprising the nucleic acid construct of paragraph 54.

[56] A recombinant host cell comprising the nucleic acid construct of paragraph 54.

[57] A method of producing a protein, comprising: (a) cultivating the recombinant host cell of paragraph 56 under conditions conducive for production of the protein; and (b) recovering the protein.

[58] A composition comprising the polypeptide of any of paragraphs 1-29.

[59] The composition of paragraph 58, which is a cellulolytic enzyme composition or a detergent composition.

[60] A method for degrading or converting a cellulosic material, comprising: treating the cellulosic material with an enzyme composition in the presence of the polypeptide having cellulolytic enhancing activity of any of paragraphs 1-29.

[61] The method of paragraph 60, wherein the cellulosic material is pretreated.

[62] The method of paragraph 60 or 61, wherein the enzyme composition comprises one or more (e.g., several) cellulolytic enzymes or cellulases selected from the group consisting of an endoglucanase, a cellobiohydrolase, and a beta-glucosidase.

[63] The method of any of paragraphs 60-62, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin; preferably the hemicellulase is one or more enzymes selected from the group consisting of a xylanase, an acetylxylan esterase, a feruloyl esterase, an arabinofuranosidase, a xylosidase, and a glucuronidase.

[64] The method of any of paragraphs 60-63, further comprising recovering the degraded cellulosic material.

[65] The method of paragraph 64, wherein the degraded cellulosic material is a sugar.

[66] The method of paragraph 65, wherein the sugar is selected from the group consisting of glucose, xylose, mannose, galactose, and arabinose.

[67] A method for producing a fermentation product, comprising: (a) saccharifying a cellulosic material with an enzyme composition in the presence of the polypeptide having cellulolytic enhancing activity of any of paragraphs 1-29; (b) fermenting the saccharified cellulosic material with one or more (e.g., several) fermenting microorganisms to produce the fermentation product; and (c) recovering the fermentation product from the fermentation.

[68] The method of paragraph 67, wherein the cellulosic material is pretreated.

[69] The method of paragraph 67 or 68, wherein the enzyme composition comprises one or more (e.g., several) cellulolytic enzymes or cellulases selected from the group consisting of an endoglucanase, a cellobiohydrolase, and a beta-glucosidase.

[70] The method of any of paragraphs 67-69, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin; preferably the hemicellulase is one or more enzymes selected from the group consisting of a xylanase, an acetylxylan esterase, a feruloyl esterase, an arabinofuranosidase, a xylosidase, and a glucuronidase.

[71] The method of any of paragraphs 67-70, wherein steps (a) and (b) are performed simultaneously in a simultaneous saccharification and fermentation.

[72] The method of any of paragraphs 69-71, wherein the fermentation product is an alcohol, an alkane, a cycloalkane, an alkene, an amino acid, a gas, isoprene, a ketone, an organic acid, or polyketide.

[73] A method of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of any of paragraphs 1-29.

[74] The method of paragraph 73, wherein the fermenting of the cellulosic material produces a fermentation product.

[75] The method of paragraph 73 or 74, further comprising recovering the fermentation product from the fermentation.

[76] The method of any of paragraphs 73-75, wherein the cellulosic material is pretreated before saccharification.

[77] The method of any of paragraphs 73-76, wherein the enzyme composition comprises one or more (e.g., several) cellulolytic enzymes or cellulases selected from the group consisting of an endoglucanase, a cellobiohydrolase, and a beta-glucosidase.

[78] The method of any of paragraphs 73-77, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin; preferably the hemicellulase is one or more enzymes selected from the group consisting of a xylanase, an acetylxylan esterase, a feruloyl esterase, an arabinofuranosidase, a xylosidase, and a glucuronidase.

[79] The method of any of paragraphs 73-78, wherein the fermentation product is an alcohol, an alkane, a cycloalkane, an alkene, an amino acid, a gas, isoprene, a ketone, an organic acid, or polyketide.

[80] A whole broth formulation or cell culture composition comprising the polypeptide of any of paragraphs 1-13.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method for producing a fermentation product, comprising:
   (a) saccharifying a cellulosic material with an enzyme composition in the presence of a GH61 polypeptide having cellulolytic enhancing activity;
   (b) fermenting the saccharified cellulosic material with one or more fermenting microorganisms to produce the fermentation product; and
   (c) recovering the fermentation product from the fermentation;
   wherein the GH61 polypeptide having cellulolytic enhancing activity is selected from the group consisting of:
   (i) a GH61 polypeptide having at least 90% sequence identity to the mature polypeptide of SEQ ID NO: 2, the mature polypeptide of SEQ ID NO: 4, or the mature polypeptide of SEQ ID NO: 6;
   (ii) a GH61 polypeptide encoded by a polynucleotide that hybridizes under at least high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.;
   (iii) a GH61 polypeptide encoded by a polynucleotide having at least 90% sequence identity to the mature polypeptide coding sequence of SEQ ID NO: 1 or the cDNA sequence thereof, the mature polypeptide coding sequence of SEQ ID NO: 3 or the cDNA sequence thereof, or the mature polypeptide coding sequence of SEQ ID NO: 5 or the cDNA sequence thereof; and
   (iv) a fragment of the polypeptide of (i), (ii), or (iii), that has cellulolytic enhancing activity.

2. The method of claim 1, wherein the cellulosic material is pretreated.

3. The method of claim 1, wherein steps (a) and (b) are performed simultaneously in a simultaneous saccharification and fermentation.

4. The method of claim 1, wherein the enzyme composition comprises one or more enzymes selected from the group consisting of a cellulase, a GH61 polypeptide, a hemicellulase, an esterase, an expansin, a laccase, a ligninolytic enzyme, a pectinase, a peroxidase, a protease, and a swollenin.

5. The method of claim 4, wherein the cellulase is one or more enzymes selected from the group consisting of an endoglucanase, a cellobiohydrolase, and a beta-glucosidase.

6. The method of claim 4, wherein the hemicellulase is one or more enzymes selected from the group consisting of a xylanase, an acetylxylan esterase, a feruloyl esterase, an arabinofuranosidase, a xylosidase, and a glucuronidase.

7. The method of claim 1, wherein the fermentation product is an alcohol, an alkane, a cycloalkane, an alkene, an amino acid, a gas, isoprene, a ketone, an organic acid, or polyketide.

8. The method of claim 1, wherein the GH61 polypeptide has at least 95% sequence identity to the mature polypeptide of SEQ ID NO: 2, the mature polypeptide of SEQ ID NO: 4, or the mature polypeptide of SEQ ID NO: 6.

9. The method of claim 1, wherein the GH61 polypeptide comprises the amino acid sequence of SEQ ID NO: 2, SEQ ID NO: 4, or SEQ ID NO: 6 or the mature polypeptide of SEQ ID NO: 2, SEQ ID NO: 4, or SEQ ID NO: 6; or a fragment thereof having cellulolytic enhancing activity.

10. The method of claim 1, wherein the GH61 polypeptide is encoded by a polynucleotide having at least 95% sequence identity to the mature polypeptide coding sequence of SEQ ID NO: 1 or the cDNA sequence thereof, the mature polypeptide coding sequence of SEQ ID NO: 3 or the cDNA sequence thereof, or the mature polypeptide coding sequence of SEQ ID NO: 5 or the cDNA sequence thereof.

11. The method of claim 1, wherein the GH61 polypeptide is encoded by a polynucleotide comprising the mature polypeptide coding sequence of SEQ ID NO: 1 or the cDNA sequence thereof, the mature polypeptide coding sequence of SEQ ID NO: 3 or the cDNA sequence thereof, or the mature polypeptide coding sequence of SEQ ID NO: 5 or the cDNA sequence thereof.

12. A method of fermenting a cellulosic material, comprising: fermenting the cellulosic material with one or more fermenting microorganisms, wherein the cellulosic material is saccharified with an enzyme composition in the presence of a polypeptide having cellulolytic enhancing activity, wherein the GH61 polypeptide having cellulolytic enhancing activity is selected from the group consisting of:
   (a) a GH61 polypeptide having at least 90% sequence identity to the mature polypeptide of SEQ ID NO: 2, the mature polypeptide of SEQ ID NO: 4, or the mature polypeptide of SEQ ID NO: 6;
   (b) a GH61 polypeptide encoded by a polynucleotide that hybridizes under at least high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1, SEQ ID NO: 3, or SEQ ID NO: 5, or (iii) a full-length complementary strand of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 65° C.;
   (c) a GH61 polypeptide encoded by a polynucleotide having at least 90% sequence identity to the mature polypeptide coding sequence of SEQ ID NO: 1 or the cDNA sequence thereof, the mature polypeptide coding sequence of SEQ ID NO: 3 or the cDNA sequence thereof, or the mature polypeptide coding sequence of SEQ ID NO: 5 or the cDNA sequence thereof; and
   (d) a fragment of the polypeptide of (a), (b), or (c), that has cellulolytic enhancing activity.

13. The method of claim 12, wherein the cellulosic material is pretreated.

14. The method of claim 12, wherein the enzyme composition comprises one or more enzymes selected from the group consisting of a cellulase, a GH61 polypeptide, a hemicellulase, an esterase, an expansin, a laccase, a ligninolytic enzyme, a pectinase, a peroxidase, a protease, and a swollenin.

15. The method of claim 14, wherein the cellulase is one or more enzymes selected from the group consisting of an endoglucanase, a cellobiohydrolase, and a beta-glucosidase.

16. The method of claim 14, wherein the hemicellulase is one or more enzymes selected from the group consisting of a xylanase, an acetylxylan esterase, a feruloyl esterase, an arabinofuranosidase, a xylosidase, and a glucuronidase.

17. The method of claim 12, wherein the fermenting of the cellulosic material produces a fermentation product.

18. The method of claim 17, further comprising recovering the fermentation product from the fermentation.

19. The method of claim 18, wherein the fermentation product is an alcohol, an alkane, a cycloalkane, an alkene, an amino acid, a gas, isoprene, a ketone, an organic acid, or polyketide.

20. The method of claim 12, wherein the GH61 polypeptide has at least 95% sequence identity to the mature polypeptide of SEQ ID NO: 2, the mature polypeptide of SEQ ID NO: 4, or the mature polypeptide of SEQ ID NO: 6.

21. The method of claim 12, wherein the GH61 polypeptide comprises the amino acid sequence of SEQ ID NO: 2, SEQ ID NO: 4, or SEQ ID NO: 6 or the mature polypeptide of SEQ ID NO: 2, SEQ ID NO: 4, or SEQ ID NO: 6; or a fragment thereof having cellulolytic enhancing activity.

22. The method of claim 12, wherein the GH61 polypeptide is encoded by a polynucleotide having at least 95% sequence identity to the mature polypeptide coding sequence of SEQ ID NO: 1 or the cDNA sequence thereof, the mature polypeptide coding sequence of SEQ ID NO: 3 or the cDNA sequence thereof, or the mature polypeptide coding sequence of SEQ ID NO: 5 or the cDNA sequence thereof.

23. The method of claim 12, wherein the GH61 polypeptide is encoded by a polynucleotide comprising the mature polypeptide coding sequence of SEQ ID NO: 1 or the cDNA sequence thereof, the mature polypeptide coding sequence of SEQ ID NO: 3 or the cDNA sequence thereof, or the mature polypeptide coding sequence of SEQ ID NO: 5 or the cDNA sequence thereof.

24. The method of claim 1, wherein the GH61 polypeptide has at least 91% sequence identity to the mature polypeptide of SEQ ID NO: 2, the mature polypeptide of SEQ ID NO: 4, or the mature polypeptide of SEQ ID NO: 6.

25. The method of claim 1, wherein the GH61 polypeptide has at least 92% sequence identity to the mature polypeptide of SEQ ID NO: 2, the mature polypeptide of SEQ ID NO: 4, or the mature polypeptide of SEQ ID NO: 6.

26. The method of claim 1, wherein the GH61 polypeptide has at least 93% sequence identity to the mature polypeptide of SEQ ID NO: 2, the mature polypeptide of SEQ ID NO: 4, or the mature polypeptide of SEQ ID NO: 6.

27. The method of claim 1, wherein the GH61 polypeptide has at least 94% sequence identity to the mature polypeptide of SEQ ID NO: 2, the mature polypeptide of SEQ ID NO: 4, or the mature polypeptide of SEQ ID NO: 6.

28. The method of claim 1, wherein the GH61 polypeptide has at least 96% sequence identity to the mature polypeptide of SEQ ID NO: 2, the mature polypeptide of SEQ ID NO: 4, or the mature polypeptide of SEQ ID NO: 6.

29. The method of claim 1, wherein the GH61 polypeptide has at least 97% sequence identity to the mature polypeptide of SEQ ID NO: 2, the mature polypeptide of SEQ ID NO: 4, or the mature polypeptide of SEQ ID NO: 6.

30. The method of claim 1, wherein the GH61 polypeptide has at least 98% sequence identity to the mature polypeptide of SEQ ID NO: 2, the mature polypeptide of SEQ ID NO: 4, or the mature polypeptide of SEQ ID NO: 6.

31. The method of claim 1, wherein the GH61 polypeptide has at least 99% sequence identity to the mature polypeptide of SEQ ID NO: 2, the mature polypeptide of SEQ ID NO: 4, or the mature polypeptide of SEQ ID NO: 6.

32. The method of claim 12, wherein the GH61 polypeptide has at least 91% sequence identity to the mature polypeptide of SEQ ID NO: 2, the mature polypeptide of SEQ ID NO: 4, or the mature polypeptide of SEQ ID NO: 6.

33. The method of claim 12, wherein the GH61 polypeptide has at least 92% sequence identity to the mature polypeptide of SEQ ID NO: 2, the mature polypeptide of SEQ ID NO: 4, or the mature polypeptide of SEQ ID NO: 6.

34. The method of claim 12, wherein the GH61 polypeptide has at least 93% sequence identity to the mature polypeptide of SEQ ID NO: 2, the mature polypeptide of SEQ ID NO: 4, or the mature polypeptide of SEQ ID NO: 6.

35. The method of claim 12, wherein the GH61 polypeptide has at least 94% sequence identity to the mature polypeptide of SEQ ID NO: 2, the mature polypeptide of SEQ ID NO: 4, or the mature polypeptide of SEQ ID NO: 6.

36. The method of claim 12, wherein the GH61 polypeptide has at least 96% sequence identity to the mature polypeptide of SEQ ID NO: 2, the mature polypeptide of SEQ ID NO: 4, or the mature polypeptide of SEQ ID NO: 6.

37. The method of claim 12, wherein the GH61 polypeptide has at least 97% sequence identity to the mature polypeptide of SEQ ID NO: 2, the mature polypeptide of SEQ ID NO: 4, or the mature polypeptide of SEQ ID NO: 6.

38. The method of claim 12, wherein the GH61 polypeptide has at least 98% sequence identity to the mature polypeptide of SEQ ID NO: 2, the mature polypeptide of SEQ ID NO: 4, or the mature polypeptide of SEQ ID NO: 6.

39. The method of claim 12, wherein the GH61 polypeptide has at least 99% sequence identity to the mature polypeptide of SEQ ID NO: 2, the mature polypeptide of SEQ ID NO: 4, or the mature polypeptide of SEQ ID NO: 6.

* * * * *

SEQUENCE LISTING

```
<160> NUMBER OF SEQ ID NOS: 12

<210> SEQ ID NO 1
<211> LENGTH: 872
<212> TYPE: DNA
```

<213> ORGANISM: Thermomyces lanuginosus

<400> SEQUENCE: 1

```
atgaagggct ccagcgctgc gtcggtgctt cttaccttcc tcgcgggcat ctcccgtacc      60
tctgcgcacg gtatgtctc caacctcgtt atcaacggcg tctactatcg ggctggctc       120
cccggcgaag accoctacaa ccctgacccc ccgattggcg ttggctggga gacgcccaac     180
ctgggcaacg gcttcgtgac gccgtcggaa gcgtcgaccg acgccgtcat ctgccacaag     240
gaagccacac cagcccgcgg tcatgtctcc gtgaaggccg gtgacaagat ctacatccaa     300
tggcagccga atccatggcc ggattccac acggtgcgt caaacttctg cccgaaagct       360
gttcacactc actaacaaca cttttaggcc ccgtcctgga ctatctggcc ccttgcaacg     420
ggccctgtga gtccgtcgac aagaccagcc tgcgcttctt caagatcgac ggagtgggtc     480
ttatcgacgg ctcttctcct ccgggctact gggccgacga cgaactcatt gcgaacggca     540
acgggtggct ggttcagatc cccgaggaca tcaagcccgg gtaactacgtc ctgcgacacg    600
agatcatcgc cttgcacagc gccgggaacc cggacggcgc ccagctgtac ccgcagtgct    660
tcaaccttga gattacggga tccggcaccg tcgagccgga gggcgtgcca gccaccgagt    720
tctactcgcc cgatgacccg ggcatcctgg tcaacatcta cgagccctg tccacgtatg    780
aggtgccggg tccctcgctc atcccgcagg cggttcagat cgagcagtct tcgtctgcga    840
ttacggcgac gggcacgccg acgccggcat ga                                  872
```

<210> SEQ ID NO 2
<211> LENGTH: 272
<212> TYPE: PRT
<213> ORGANISM: Thermomyces lanuginosus

<400> SEQUENCE: 2

```
Met Lys Gly Ser Ser Ala Ala Ser Val Leu Leu Thr Phe Leu Ala Gly
1               5                   10                  15

Ile Ser Arg Thr Ser Ala His Gly Tyr Val Ser Asn Leu Val Ile Asn
            20                  25                  30

Gly Val Tyr Tyr Arg Gly Trp Leu Pro Gly Glu Asp Pro Tyr Asn Pro
        35                  40                  45

Asp Pro Pro Ile Gly Val Gly Trp Glu Thr Pro Asn Leu Gly Asn Gly
    50                  55                  60

Phe Val Thr Pro Ser Glu Ala Ser Thr Asp Ala Val Ile Cys His Lys
65                  70                  75                  80

Glu Ala Thr Pro Ala Arg Gly His Val Ser Val Lys Ala Gly Asp Lys
                85                  90                  95

Ile Tyr Ile Gln Trp Gln Pro Asn Pro Trp Pro Asp Ser His His Gly
            100                 105                 110

Pro Val Leu Asp Tyr Leu Ala Pro Cys Asn Gly Pro Cys Glu Ser Val
        115                 120                 125

Asp Lys Thr Ser Leu Arg Phe Phe Lys Ile Asp Gly Val Gly Leu Ile
    130                 135                 140

Asp Gly Ser Ser Pro Pro Gly Tyr Trp Ala Asp Asp Glu Leu Ile Ala
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Ser Ala Gly Asn
            180                 185                 190

Pro Asp Gly Ala Gln Leu Tyr Pro Gln Cys Phe Asn Leu Glu Ile Thr
```

```
                195                 200                 205
Gly Ser Gly Thr Val Glu Pro Glu Gly Val Pro Ala Thr Glu Phe Tyr
        210                 215                 220

Ser Pro Asp Asp Pro Gly Ile Leu Val Asn Ile Tyr Glu Pro Leu Ser
225                 230                 235                 240

Thr Tyr Glu Val Pro Gly Pro Ser Leu Ile Pro Gln Ala Val Gln Ile
                245                 250                 255

Glu Gln Ser Ser Ala Ile Thr Ala Thr Gly Thr Pro Thr Pro Ala
        260                 265                 270

<210> SEQ ID NO 3
<211> LENGTH: 1039
<212> TYPE: DNA
<213> ORGANISM: Thermomyces lanuginosus

<400> SEQUENCE: 3
atggcattct ctacggttac agttttttgtt acgttcctgg ccttcatctc catagcttct      60
gctcatggct tcgtgacaaa aatcaccgta ctcggagata taataagga gtacgtctca      120 gtctcgctag gttgctaaca caggagagat cgctgaccat tgcagctacc ccggctttga      180
cccgagcact cccaaggagg ttcctccggg tctcgatgtc gcttggtcta ctagtgccag      240
tgatcaggga tacatgagca gttcaaatgc ctcgtatcac agtaaggact ttatctgcca      300
cagaaacgcc aaacctgctc agacgcagc tcaagttcat gcgggcgaca aggtgcagct      360
tcactggact caatggcctg acctgagga tcaccagggt cctatccttg attacctcgc      420
gagctgcaac ggaccctgct caaacgtgga aaggcgagc cttaagtgga cgaagattga      480
cgaggcaggg cgcttttccca acggaacgtg ggcaacggac ctgctcagga atggggggaaa      540 cacgtggaat gtgacgattc catcggatct tgctcctgga gaatatgtcc tccgcaacga      600
gatcattgca cttcactcgg cgagaaatat gggtggagct cagcactaca tgcaatgtgt      660
caatctgaac gtcactggca ccggccatag agagctacag gcgtctccg ccgcagaatt      720 ttacaatcct acggatcctg gaattttgat taacgtctgg caaactcaaa gccttttcctc      780 ctaccatatt cccggaccta cactgttagc cgccgatacc ggcaacgacg gtggccattc      840
tgcatcatct accttggcga ctgtgacaag cagacgtctt tccactccga gcgacgccat      900
gcccgggaat ggttcatacg gtgcaatttc gccgccctc aaacctgcta aggattcca      960 tcctgttttgt aacgcccgat tcagacatgg cagcactttc actttgacta ccctggtcgc     1020
accaccagcc aggacctaa                                                    1039

<210> SEQ ID NO 4
<211> LENGTH: 327
<212> TYPE: PRT
<213> ORGANISM: Thermomyces lanuginosus

<400> SEQUENCE: 4

Met Ala Phe Ser Thr Val Thr Val Phe Val Thr Phe Leu Ala Phe Ile
1               5                   10                  15

Ser Ile Ala Ser Ala His Gly Phe Val Thr Lys Ile Thr Val Leu Gly
            20                  25                  30

Asp Asn Asn Lys Asp Tyr Pro Gly Phe Asp Pro Ser Thr Pro Lys Glu
        35                  40                  45

Val Pro Pro Gly Leu Asp Val Ala Trp Ser Thr Ser Ala Ser Asp Gln
50                  55                  60

Gly Tyr Met Ser Ser Ser Asn Ala Ser Tyr His Ser Lys Asp Phe Ile
```

```
            65                  70                  75                  80
Cys His Arg Asn Ala Lys Pro Ala Pro Asp Ala Ala Gln Val His Ala
                85                  90                  95

Gly Asp Lys Val Gln Leu His Trp Thr Gln Trp Pro Gly Pro Glu Asp
            100                 105                 110

His Gln Gly Pro Ile Leu Asp Tyr Leu Ala Ser Cys Asn Gly Pro Cys
        115                 120                 125

Ser Asn Val Glu Lys Ala Ser Leu Lys Trp Thr Lys Ile Asp Glu Ala
    130                 135                 140

Gly Arg Phe Pro Asn Gly Thr Trp Ala Thr Asp Leu Leu Arg Asn Gly
145                 150                 155                 160

Gly Asn Thr Trp Asn Val Thr Ile Pro Ser Asp Leu Ala Pro Gly Glu
                165                 170                 175

Tyr Val Leu Arg Asn Glu Ile Ile Ala Leu His Ser Ala Arg Asn Met
            180                 185                 190

Gly Gly Ala Gln His Tyr Met Gln Cys Val Asn Leu Asn Val Thr Gly
        195                 200                 205

Thr Gly His Arg Glu Leu Gln Gly Val Ser Ala Ala Glu Phe Tyr Asn
    210                 215                 220

Pro Thr Asp Pro Gly Ile Leu Ile Asn Val Trp Gln Thr Gln Ser Leu
225                 230                 235                 240

Ser Ser Tyr His Ile Pro Gly Pro Thr Leu Leu Ala Ala Asp Thr Gly
                245                 250                 255

Asn Asp Gly Gly His Ser Ala Ser Ser Thr Leu Ala Thr Val Thr Ser
            260                 265                 270

Arg Arg Leu Ser Thr Pro Ser Asp Ala Met Pro Gly Asn Gly Ser Tyr
        275                 280                 285

Gly Ala Ile Ser Pro Pro Leu Lys Pro Ala Lys Gly Phe His Pro Val
    290                 295                 300

Cys Asn Ala Arg Phe Arg His Gly Ser Thr Phe Thr Leu Thr Thr Leu
305                 310                 315                 320

Val Ala Pro Pro Ala Arg Thr
                325

<210> SEQ ID NO 5
<211> LENGTH: 881
<212> TYPE: DNA
<213> ORGANISM: Thermomyces lanuginosus

<400> SEQUENCE: 5
atgaaaggct ccaccactgc gtctttgctt cttccgctcc tggcgagcgt tactcgcacc    60
tctgcgcacg ggtttgtctc caacctcgtc atcaatggcg tcttctatcg gggctggctc   120
ccgaccgagg accctacaa ggctgacccc ccgattggcg tcggctggga gacgcctaac   180
ctgggcaacg gcttcgtgct gcccgaagaa gcgtcgaccg atgccatcgt ctgccacaaa   240
gaggccgagc cggcccgcgg ctatgccagc gtcgctgccg gtgacaagat ctacattcag   300
tggcagccga acccatggcc ggagtctcat cacggtacgt caaactgccc attgttgcaa   360
ttcagaatca tctactaaca actcttcaag gccccgtcat tgactacctg gccccttgca   420
acggtgactg ctcgactgtc aacaagacca gtttggagtt cttcaagatc gacggcgtgg   480
gcctcatcga cggctcctcc ccgccgggta agtgggctga cgacgagctc attgccaacg   540
gcaacggctg gctggtccag atccccgagg acatcaagcc gggcaactac gtcctgcgcc   600
atgagatcat cgccttgcac gaggcgttca accagaacgg cgctcagatc tacccgcagt   660
```

```
gcttcaacct ccagattacc ggctccggca ctgtcgagcc cgagggcacg ccggctaccg    720
agctgtattc gcccaccgat ccgggcattc tggttgacat ctacaacccc ttgagcacgt    780
acgtcgtgcc cggcccgacg ctcatcccgc aggcggttga gattgagcag tcttcgtcgg    840
ctgtcacggc gactggtacg ccgacgccgg cggcggcgta a                        881
```

<210> SEQ ID NO 6
<211> LENGTH: 274
<212> TYPE: PRT
<213> ORGANISM: Thermomyces lanuginosus

<400> SEQUENCE: 6

```
Met Lys Gly Ser Thr Thr Ala Ser Leu Leu Pro Leu Leu Ala Ser
1               5                   10                  15

Val Thr Arg Thr Ser Ala His Gly Phe Val Ser Asn Leu Val Ile Asn
            20                  25                  30

Gly Val Phe Tyr Arg Gly Trp Leu Pro Thr Glu Asp Pro Tyr Lys Ala
        35                  40                  45

Asp Pro Pro Ile Gly Val Gly Trp Glu Thr Pro Asn Leu Gly Asn Gly
    50                  55                  60

Phe Val Leu Pro Glu Glu Ala Ser Thr Asp Ala Ile Val Cys His Lys
65                  70                  75                  80

Glu Ala Glu Pro Ala Arg Gly Tyr Ala Ser Val Ala Ala Gly Asp Lys
                85                  90                  95

Ile Tyr Ile Gln Trp Gln Pro Asn Pro Trp Pro Glu Ser His His Gly
            100                 105                 110

Pro Val Ile Asp Tyr Leu Ala Pro Cys Asn Gly Asp Cys Ser Thr Val
        115                 120                 125

Asn Lys Thr Ser Leu Glu Phe Phe Lys Ile Asp Gly Val Gly Leu Ile
    130                 135                 140

Asp Gly Ser Ser Pro Gly Lys Trp Ala Asp Glu Leu Ile Ala
145                 150                 155                 160

Asn Gly Asn Gly Trp Leu Val Gln Ile Pro Glu Asp Ile Lys Pro Gly
                165                 170                 175

Asn Tyr Val Leu Arg His Glu Ile Ile Ala Leu His Glu Ala Phe Asn
            180                 185                 190

Gln Asn Gly Ala Gln Ile Tyr Pro Gln Cys Phe Asn Leu Gln Ile Thr
        195                 200                 205

Gly Ser Gly Thr Val Glu Pro Glu Gly Thr Pro Ala Thr Glu Leu Tyr
    210                 215                 220

Ser Pro Thr Asp Pro Gly Ile Leu Val Asp Ile Tyr Asn Pro Leu Ser
225                 230                 235                 240

Thr Tyr Val Val Pro Gly Pro Thr Leu Ile Pro Gln Ala Val Glu Ile
                245                 250                 255

Glu Gln Ser Ser Ser Ala Val Thr Ala Thr Gly Thr Pro Thr Pro Ala
            260                 265                 270

Ala Ala
```

```
<210> SEQ ID NO 7
<211> LENGTH: 38
<212> TYPE: DNA
<213> ORGANISM: Artificial Sequence
<220> FEATURE:
<223> OTHER INFORMATION: Synthetic Construct

<400> SEQUENCE: 7
acacaactgg ggatccacca tgaagggctc cagcgctg                               38

<210> SEQ ID NO 8
<211> LENGTH: 40
<212> TYPE: DNA
<213> ORGANISM: Artificial Sequence
<220> FEATURE:
<223> OTHER INFORMATION: Synthetic Construct

<400> SEQUENCE: 8
gtcaccctct agatctctca acgcaccatg tactcgtctc                             40

<210> SEQ ID NO 9
<211> LENGTH: 51
<212> TYPE: DNA
<213> ORGANISM: Artificial Sequence
<220> FEATURE:
<223> OTHER INFORMATION: Synthetic Construct

<400> SEQUENCE: 9
acacaactgg ggatccacca tggcattctc tacggttaca gttttttgtta c               51

<210> SEQ ID NO 10
<211> LENGTH: 43
<212> TYPE: DNA
<213> ORGANISM: Artificial Sequence
<220> FEATURE:
<223> OTHER INFORMATION: Synthetic Construct

<400> SEQUENCE: 10
gtcaccctct agatctaatg agagagcata tccataaccg cat                         43

<210> SEQ ID NO 11
<211> LENGTH: 40
<212> TYPE: DNA
<213> ORGANISM: Artificial Sequence
<220> FEATURE:
<223> OTHER INFORMATION: Synthetic Construct

<400> SEQUENCE: 11
acacaactgg ggatccacca tgaaaggctc caccactgcg                             40

<210> SEQ ID NO 12
<211> LENGTH: 38
<212> TYPE: DNA
<213> ORGANISM: Artificial Sequence
<220> FEATURE:
<223> OTHER INFORMATION: Synthetic Construct

<400> SEQUENCE: 12
gtcaccctct agatctcagc ggtagcaagc attcgact                               38
```